(12) United States Patent
Hossainy et al.

(10) Patent No.: US 7,297,159 B2
(45) Date of Patent: Nov. 20, 2007

(54) SELECTIVE COATING OF MEDICAL DEVICES

(75) Inventors: Syed F. A. Hossainy, Fremont, CA (US); Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/897,244

(22) Filed: Jul. 21, 2004

(65) Prior Publication Data
US 2004/0265475 A1 Dec. 30, 2004

Related U.S. Application Data

(62) Division of application No. 09/697,106, filed on Oct. 26, 2000, now Pat. No. 6,783,793.

(51) Int. Cl.
*A61F 2/06* (2006.01)
(52) U.S. Cl. .................. 623/1.46; 623/1.42; 427/2.24; 427/2.25
(58) Field of Classification Search ............... 427/2.24, 427/2.25; 623/1.39, 1.42, 1.43, 1.44, 1.45, 623/1.46
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 2,647,017 A | 7/1953 | Coulliette | |
| 2,701,559 A | 2/1955 | Cooper | |
| 3,288,728 A | 11/1966 | Gorham | |
| 3,687,135 A | 8/1972 | Stroganov et al. | |

(Continued)

FOREIGN PATENT DOCUMENTS

CA   2 008 312   7/1990

(Continued)

OTHER PUBLICATIONS

Barath et al., *Low Dose of Antitumor Agents Prevents Smooth Muscle Cell Proliferation After Endothelial Injury*, JACC 13(2):252A (1989) (Abstract).

(Continued)

*Primary Examiner*—Corrine McDermott
*Assistant Examiner*—Javier G. Blanco
(74) *Attorney, Agent, or Firm*—Squire, Sanders & Dempsey LLP

(57) ABSTRACT

Methods for coating different regions of an implantable device are disclosed. An embodiment of the method includes dipping a first portion of the implantable device into a first coating substance, and then centrifuging the implantable device to provide an even coating. Next, a second portion of the implantable device is dipped into a second coating substance, and the implantable device is again centrifuged, resulting in an even second coating. In another embodiment, a first coating substance is applied to an interior surface of a cylindrical implantable device, such as a stent or graft, and a second coating substance is applied to an exterior surface. A centrifuge step is performed so that the first coating substance is preferentially and uniformly applied on the interior surface of the implantable device and the second coating substance is preferentially and uniformly applied on the exterior surface of the implantable device.

11 Claims, 4 Drawing Sheets

U.S. PATENT DOCUMENTS

| | | |
|---|---|---|
| 3,773,737 A | 11/1973 | Goodman et al. |
| 3,839,743 A | 10/1974 | Schwarcz |
| 3,849,514 A | 11/1974 | Gray, Jr. et al. |
| 3,900,632 A | 8/1975 | Robinson |
| 4,075,045 A | 2/1978 | Rideout |
| 4,104,410 A | 8/1978 | Malecki |
| 4,110,497 A | 8/1978 | Hoel |
| 4,132,357 A | 1/1979 | Blackinton |
| 4,164,524 A | 8/1979 | Ward et al. |
| 4,226,243 A | 10/1980 | Shalaby et al. |
| 4,321,711 A | 3/1982 | Mano |
| 4,323,071 A | 4/1982 | Simpson et al. |
| 4,329,383 A | 5/1982 | Joh |
| 4,338,942 A | 7/1982 | Fogarty |
| 4,343,931 A | 8/1982 | Barrows |
| 4,346,028 A | 8/1982 | Griffith |
| 4,439,185 A | 3/1984 | Lundquist |
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,573,470 A | 3/1986 | Samson et al. |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo |
| 4,633,873 A | 1/1987 | Dumican et al. |
| 4,638,805 A | 1/1987 | Powell |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,768,507 A | 9/1988 | Fischell et al. |
| 4,774,039 A | 9/1988 | Wrasidlo |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,828,561 A | 5/1989 | Woodroof |
| 4,850,999 A | 7/1989 | Planck |
| 4,865,870 A | 9/1989 | Hu et al. |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor |
| 4,902,289 A | 2/1990 | Yannas |
| 4,906,423 A | 3/1990 | Frisch |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,977,901 A | 12/1990 | Ofstead |
| 4,988,356 A | 1/1991 | Crittenden et al. |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,019,090 A | 5/1991 | Pinchuk |
| 5,019,096 A | 5/1991 | Fox, Jr. et al. |
| 5,028,597 A | 7/1991 | Kodama et al. |
| 5,037,392 A | 8/1991 | Hillstead |
| 5,037,427 A | 8/1991 | Harada et al. |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky |
| 5,087,394 A | 2/1992 | Keith |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf |
| 5,176,638 A | 1/1993 | Don Michael |
| 5,188,734 A | 2/1993 | Zepf |
| 5,192,311 A | 3/1993 | King et al. |
| 5,197,977 A | 3/1993 | Hoffman, Jr. et al. |
| 5,205,822 A | 4/1993 | Johnson et al. |
| 5,213,561 A | 5/1993 | Weinstein et al. |
| 5,213,576 A | 5/1993 | Abiuso et al. |
| 5,219,980 A | 6/1993 | Swidler |
| 5,222,971 A | 6/1993 | Willard et al. |
| 5,225,750 A | 7/1993 | Higuchi et al. |
| 5,226,889 A | 7/1993 | Sheiban |
| 5,226,913 A | 7/1993 | Pinchuk |
| 5,229,045 A | 7/1993 | Soldani |
| 5,229,172 A | 7/1993 | Cahalan et al. |
| 5,232,444 A | 8/1993 | Just |
| 5,234,456 A | 8/1993 | Silvestrini |
| 5,234,457 A | 8/1993 | Andersen |
| 5,236,447 A | 8/1993 | Kubo et al. |
| 5,242,399 A | 9/1993 | Lau et al. |
| 5,254,089 A | 10/1993 | Wang |
| 5,254,091 A | 10/1993 | Aliahmad et al. |
| 5,258,020 A | 11/1993 | Froix |
| 5,258,419 A | 11/1993 | Rolando et al. |

| | | | | | |
|---|---|---|---|---|---|
| 5,269,802 A | 12/1993 | Garber | 5,476,476 A | 12/1995 | Hillstead |
| 5,272,012 A | 12/1993 | Opolski | 5,476,509 A | 12/1995 | Keogh et al. |
| 5,278,200 A | 1/1994 | Coury et al. | 5,485,496 A | 1/1996 | Lee et al. |
| 5,279,594 A | 1/1994 | Jackson | 5,496,346 A | 3/1996 | Horzewski et al. |
| 5,282,823 A | 2/1994 | Schwartz et al. | 5,500,013 A | 3/1996 | Buscemi et al. |
| 5,282,860 A | 2/1994 | Matsuno et al. | 5,501,227 A | 3/1996 | Yock |
| 5,286,254 A | 2/1994 | Shapland et al. | 5,502,158 A | 3/1996 | Sinclair et al. |
| 5,289,831 A | 3/1994 | Bosley | 5,507,768 A | 4/1996 | Lau et al. |
| 5,290,271 A | 3/1994 | Jernberg | 5,511,726 A | 4/1996 | Greenspan et al. |
| 5,292,516 A | 3/1994 | Viegas et al. | 5,514,154 A | 5/1996 | Lau et al. |
| 5,298,260 A | 3/1994 | Viegas et al. | 5,514,379 A | 5/1996 | Weissleder et al. |
| 5,300,295 A | 4/1994 | Viegas et al. | 5,516,560 A | 5/1996 | Harayama et al. |
| 5,304,200 A | 4/1994 | Spaulding | 5,516,881 A | 5/1996 | Lee et al. |
| 5,306,250 A | 4/1994 | March et al. | 5,527,337 A | 6/1996 | Stack et al. |
| 5,306,286 A | 4/1994 | Stack et al. | 5,537,729 A | 7/1996 | Kolobow |
| 5,306,294 A | 4/1994 | Winston et al. | 5,538,493 A | 7/1996 | Gerken et al. |
| 5,306,501 A | 4/1994 | Viegas et al. | 5,545,209 A | 8/1996 | Roberts et al. |
| 5,306,786 A | 4/1994 | Moens et al. | 5,545,408 A | 8/1996 | Trigg et al. |
| 5,308,641 A | 5/1994 | Cahalan et al. | 5,551,954 A | 9/1996 | Buscemi et al. |
| 5,314,472 A | 5/1994 | Fontaine | 5,554,120 A | 9/1996 | Chen et al. |
| 5,318,531 A | 6/1994 | Leone | 5,554,182 A | 9/1996 | Dinh et al. |
| 5,328,471 A | 7/1994 | Slepian | 5,556,413 A | 9/1996 | Lam |
| 5,330,500 A | 7/1994 | Song | 5,558,642 A | 9/1996 | Schweich, Jr. et al. |
| 5,330,768 A | 7/1994 | Park et al. | 5,562,728 A | 10/1996 | Lazarus et al. |
| 5,336,518 A | 8/1994 | Narayanan et al. | 5,569,463 A | 10/1996 | Helmus et al. |
| 5,342,283 A | 8/1994 | Good | 5,571,135 A | 11/1996 | Fraser et al. |
| 5,342,348 A | 8/1994 | Kaplan | 5,571,166 A | 11/1996 | Dinh et al. |
| 5,342,395 A | 8/1994 | Jarrett et al. | 5,571,567 A | 11/1996 | Shah |
| 5,342,621 A | 8/1994 | Eury | 5,578,046 A | 11/1996 | Liu et al. |
| 5,344,426 A | 9/1994 | Lau et al. | 5,578,073 A | 11/1996 | Haimovich et al. |
| 5,344,455 A | 9/1994 | Keogh et al. | 5,584,877 A | 12/1996 | Miyake et al. |
| 5,350,800 A | 9/1994 | Verhoeven et al. | 5,588,962 A | 12/1996 | Nicholas et al. |
| 5,356,433 A | 10/1994 | Rowland et al. | 5,591,199 A | 1/1997 | Porter et al. |
| 5,360,401 A | 11/1994 | Turnland et al. | 5,591,224 A | 1/1997 | Schwartz et al. |
| 5,360,443 A | 11/1994 | Barone et al. | 5,591,227 A | 1/1997 | Dinh et al. |
| 5,364,354 A | 11/1994 | Walker et al. | 5,591,607 A | 1/1997 | Gryaznov et al. |
| 5,366,504 A | 11/1994 | Andersen et al. | 5,593,403 A | 1/1997 | Buscemi |
| 5,368,560 A | 11/1994 | Rambo et al. | 5,593,434 A | 1/1997 | Williams |
| 5,370,684 A | 12/1994 | Vallana et al. | 5,595,722 A | 1/1997 | Grainger et al. |
| 5,380,299 A | 1/1995 | Fearnot et al. | 5,599,301 A | 2/1997 | Jacobs et al. |
| 5,383,925 A | 1/1995 | Schmitt | 5,599,307 A | 2/1997 | Bacher et al. |
| 5,383,927 A | 1/1995 | DeGoicoechea et al. | 5,599,352 A | 2/1997 | Dinh et al. |
| 5,385,580 A | 1/1995 | Schmitt | 5,599,922 A | 2/1997 | Gryaznov et al. |
| 5,387,450 A | 2/1995 | Stewart | 5,605,696 A | 2/1997 | Eury et al. |
| 5,389,106 A | 2/1995 | Tower | 5,607,442 A | 3/1997 | Fischell et al. |
| 5,399,666 A | 3/1995 | Ford | 5,607,467 A | 3/1997 | Froix |
| 5,405,472 A | 4/1995 | Leone | 5,609,629 A | 3/1997 | Fearnot et al. |
| 5,409,495 A | 4/1995 | Osborn | 5,610,241 A | 3/1997 | Lee et al. |
| 5,411,466 A | 5/1995 | Hess | 5,611,775 A | 3/1997 | Machold et al. |
| 5,411,477 A | 5/1995 | Saab | 5,616,338 A | 4/1997 | Fox, Jr. et al. |
| 5,412,035 A | 5/1995 | Schmitt et al. | 5,618,298 A | 4/1997 | Simon |
| 5,415,938 A | 5/1995 | Cahalan et al. | 5,618,299 A | 4/1997 | Khosravi et al. |
| 5,417,981 A | 5/1995 | Endo et al. | 5,620,420 A | 4/1997 | Kriesel |
| 5,423,849 A | 6/1995 | Engelson et al. | 5,624,411 A | 4/1997 | Tuch |
| 5,423,885 A | 6/1995 | Williams | 5,628,730 A | 5/1997 | Shapland et al. |
| 5,429,618 A | 7/1995 | Keogh | 5,628,755 A | 5/1997 | Heller et al. |
| 5,441,515 A | 8/1995 | Khosravi et al. | 5,628,781 A | 5/1997 | Williams et al. |
| 5,443,458 A | 8/1995 | Eury et al. | 5,628,785 A | 5/1997 | Schwartz et al. |
| 5,443,496 A | 8/1995 | Schwartz et al. | 5,628,786 A | 5/1997 | Banas et al. |
| 5,443,500 A | 8/1995 | Sigwart | 5,629,077 A | 5/1997 | Turnlund et al. |
| 5,445,646 A | 8/1995 | Euteneuer et al. | 5,631,135 A | 5/1997 | Gryaznov et al. |
| 5,447,724 A | 9/1995 | Helmus et al. | 5,632,771 A | 5/1997 | Boatman et al. |
| 5,451,233 A | 9/1995 | Yock | 5,632,840 A | 5/1997 | Campbell |
| 5,455,040 A | 10/1995 | Marchant | 5,637,113 A | 6/1997 | Tartaglia et al. |
| 5,456,661 A | 10/1995 | Narcisco, Jr. | 5,644,020 A | 7/1997 | Timmermann et al. |
| 5,456,713 A | 10/1995 | Chuter | 5,645,559 A | 7/1997 | Hachtman et al. |
| 5,458,615 A | 10/1995 | Klemm et al. | 5,649,951 A | 7/1997 | Davidson |
| 5,460,610 A | 10/1995 | Don Michael | 5,649,977 A | 7/1997 | Campbell |
| 5,462,990 A | 10/1995 | Hubbell et al. | 5,653,691 A | 8/1997 | Rupp et al. |
| 5,464,450 A | 11/1995 | Buscemi et al. | 5,656,080 A | 8/1997 | Staniforth et al. |
| 5,464,650 A | 11/1995 | Berg et al. | 5,656,082 A | 8/1997 | Takatsuki et al. |
| 5,470,313 A | 11/1995 | Crocker | 5,658,995 A | 8/1997 | Kohn et al. |
| 5,470,603 A | 11/1995 | Staniforth et al. | 5,667,523 A | 9/1997 | Bynon et al. |

| | | |
|---|---|---|
| 5,667,767 A | 9/1997 | Greff et al. |
| 5,667,796 A | 9/1997 | Otten |
| 5,670,558 A | 9/1997 | Onishi et al. |
| 5,674,242 A | 10/1997 | Phan et al. |
| 5,679,400 A | 10/1997 | Tuch |
| 5,693,085 A | 12/1997 | Buirge et al. |
| 5,693,376 A | 12/1997 | Fetherston et al. |
| 5,695,498 A | 12/1997 | Tower |
| 5,695,810 A | 12/1997 | Dubin et al. |
| 5,697,967 A | 12/1997 | Dinh et al. |
| 5,700,286 A | 12/1997 | Tartaglia et al. |
| 5,702,754 A | 12/1997 | Zhong |
| 5,702,818 A | 12/1997 | Cahalan et al. |
| 5,707,385 A | 1/1998 | Williams |
| 5,711,763 A | 1/1998 | Nonami et al. |
| 5,711,812 A | 1/1998 | Chapek et al. |
| 5,711,958 A | 1/1998 | Cohn et al. |
| 5,713,949 A | 2/1998 | Jayaraman |
| 5,716,981 A | 2/1998 | Hunter et al. |
| 5,718,726 A | 2/1998 | Amon et al. |
| 5,720,726 A | 2/1998 | Marcadis et al. |
| 5,721,131 A | 2/1998 | Rudolph et al. |
| 5,722,984 A | 3/1998 | Fischell et al. |
| 5,723,219 A | 3/1998 | Kolluri et al. |
| 5,725,549 A | 3/1998 | Lam |
| 5,726,297 A | 3/1998 | Gryaznov et al. |
| 5,728,068 A | 3/1998 | Leone et al. |
| 5,728,751 A | 3/1998 | Patnaik |
| 5,730,698 A | 3/1998 | Fischell et al. |
| 5,733,326 A | 3/1998 | Tomonto et al. |
| 5,733,327 A | 3/1998 | Igaki et al. |
| 5,733,330 A | 3/1998 | Cox |
| 5,733,564 A | 3/1998 | Lehtinen |
| 5,733,925 A | 3/1998 | Kunz et al. |
| 5,735,897 A | 4/1998 | Buirge |
| 5,741,554 A | 4/1998 | Tisone |
| 5,741,881 A | 4/1998 | Patnaik |
| 5,746,745 A | 5/1998 | Abele et al. |
| 5,746,998 A | 5/1998 | Torchilin et al. |
| 5,756,457 A | 5/1998 | Wang et al. |
| 5,756,476 A | 5/1998 | Epstein et al. |
| 5,759,205 A | 6/1998 | Valentini |
| 5,759,474 A | 6/1998 | Rupp et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,769,884 A | 6/1998 | Solovay |
| 5,770,609 A | 6/1998 | Grainger et al. |
| 5,772,864 A | 6/1998 | Møller et al. |
| 5,776,184 A | 7/1998 | Tuch |
| 5,780,807 A | 7/1998 | Saunders |
| 5,782,742 A | 7/1998 | Crocker |
| 5,783,657 A | 7/1998 | Pavlin et al. |
| 5,788,626 A | 8/1998 | Thompson |
| 5,788,979 A | 8/1998 | Alt et al. |
| 5,800,392 A | 9/1998 | Racchini |
| 5,800,516 A | 9/1998 | Fine et al. |
| 5,804,318 A | 9/1998 | Pinchuk et al. |
| 5,807,244 A | 9/1998 | Barot |
| 5,810,871 A | 9/1998 | Tuckey et al. |
| 5,810,873 A | 9/1998 | Morales |
| 5,811,151 A | 9/1998 | Hendriks et al. |
| 5,811,447 A | 9/1998 | Kunz et al. |
| 5,820,917 A | 10/1998 | Tuch |
| 5,823,996 A | 10/1998 | Sparks |
| 5,824,048 A | 10/1998 | Tuch |
| 5,824,049 A | 10/1998 | Ragheb et al. |
| 5,824,056 A | 10/1998 | Rosenberg |
| 5,826,586 A | 10/1998 | Mishra et al. |
| 5,830,178 A | 11/1998 | Jones et al. |
| 5,830,179 A | 11/1998 | Mikus et al. |
| 5,830,217 A | 11/1998 | Ryan |
| 5,830,461 A | 11/1998 | Billiar |
| 5,830,879 A | 11/1998 | Isner |
| 5,833,644 A | 11/1998 | Zadno-Azizi et al. |
| 5,833,651 A | 11/1998 | Donovan et al. |
| 5,833,659 A | 11/1998 | Kranys |
| 5,834,582 A | 11/1998 | Sinclair et al. |
| 5,836,962 A | 11/1998 | Gianotti |
| 5,836,965 A | 11/1998 | Jendersee et al. |
| 5,837,008 A | 11/1998 | Berg et al. |
| 5,837,313 A | 11/1998 | Ding et al. |
| 5,837,835 A | 11/1998 | Gryaznov et al. |
| 5,840,009 A | 11/1998 | Fischell et al. |
| 5,840,083 A | 11/1998 | Braach-Maksvytis |
| 5,843,033 A | 12/1998 | Ropiak |
| 5,843,119 A | 12/1998 | Schulewitz |
| 5,843,172 A | 12/1998 | Yan |
| 5,846,247 A | 12/1998 | Unsworth et al. |
| 5,849,859 A | 12/1998 | Acemoglu |
| 5,851,508 A | 12/1998 | Greff et al. |
| 5,853,408 A | 12/1998 | Muni |
| 5,854,207 A | 12/1998 | Lee et al. |
| 5,854,376 A | 12/1998 | Higashi |
| 5,855,598 A | 1/1999 | Pinchuk |
| 5,855,612 A | 1/1999 | Ohthuki et al. |
| 5,855,618 A | 1/1999 | Patnaik et al. |
| 5,857,998 A | 1/1999 | Barry |
| 5,858,556 A | 1/1999 | Eckhart et al. |
| 5,858,746 A | 1/1999 | Hubbell et al. |
| 5,858,990 A | 1/1999 | Walsh |
| 5,860,954 A | 1/1999 | Ropiak |
| 5,865,814 A | 2/1999 | Tuch |
| 5,866,113 A | 2/1999 | Hendriks et al. |
| 5,868,781 A | 2/1999 | Killion |
| 5,869,127 A | 2/1999 | Zhong |
| 5,871,436 A | 2/1999 | Eury |
| 5,871,437 A | 2/1999 | Alt |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,874,355 A | 2/1999 | Huang et al. |
| 5,876,426 A | 3/1999 | Kume et al. |
| 5,876,433 A | 3/1999 | Lunn |
| 5,876,743 A | 3/1999 | Ibsen et al. |
| 5,877,224 A | 3/1999 | Brocchini et al. |
| 5,877,263 A | 3/1999 | Patnaik et al. |
| 5,879,713 A | 3/1999 | Roth et al. |
| 5,883,011 A | 3/1999 | Lin et al. |
| 5,888,533 A | 3/1999 | Dunn |
| 5,891,192 A | 4/1999 | Murayama et al. |
| 5,893,840 A | 4/1999 | Hull et al. |
| 5,893,852 A | 4/1999 | Morales |
| 5,895,407 A | 4/1999 | Jayaraman |
| 5,897,911 A | 4/1999 | Loeffler |
| 5,897,955 A | 4/1999 | Drumheller |
| 5,898,178 A | 4/1999 | Bunker |
| 5,902,631 A | 5/1999 | Wang et al. |
| 5,902,875 A | 5/1999 | Roby et al. |
| 5,905,168 A | 5/1999 | Dos Santos et al. |
| 5,906,759 A | 5/1999 | Richter |
| 5,910,564 A | 6/1999 | Gruning et al. |
| 5,914,182 A | 6/1999 | Drumheller |
| 5,914,387 A | 6/1999 | Roby et al. |
| 5,916,234 A | 6/1999 | Lam |
| 5,916,870 A | 6/1999 | Lee et al. |
| 5,919,893 A | 7/1999 | Roby et al. |
| 5,921,416 A | 7/1999 | Uchara |
| 5,922,005 A | 7/1999 | Richter et al. |
| 5,922,393 A | 7/1999 | Jayaraman |
| 5,925,552 A | 7/1999 | Keogh et al. |
| 5,925,720 A | 7/1999 | Kataoka et al. |
| 5,928,916 A | 7/1999 | Keogh |

| | | | | | |
|---|---|---|---|---|---|
| 5,932,299 A | 8/1999 | Katoot | 6,096,525 A | 8/2000 | Patnaik |
| 5,935,135 A | 8/1999 | Bramfitt et al. | 6,099,455 A | 8/2000 | Columbo et al. |
| 5,942,209 A | 8/1999 | Leavitt et al. | 6,099,559 A | 8/2000 | Nolting |
| 5,947,993 A | 9/1999 | Morales | 6,099,561 A | 8/2000 | Alt |
| 5,948,018 A | 9/1999 | Dereume et al. | 6,099,562 A | 8/2000 | Ding et al. |
| 5,948,428 A | 9/1999 | Lee et al. | 6,103,230 A | 8/2000 | Billiar et al. |
| 5,951,881 A | 9/1999 | Rogers et al. | 6,106,454 A | 8/2000 | Berg et al. |
| 5,954,744 A | 9/1999 | Phan et al. | 6,106,530 A | 8/2000 | Harada |
| 5,955,509 A | 9/1999 | Webber et al. | 6,106,889 A | 8/2000 | Beavers et al. |
| 5,957,975 A | 9/1999 | Lafont et al. | 6,107,416 A | 8/2000 | Patnaik et al. |
| 5,958,385 A | 9/1999 | Tondeur et al. | 6,110,180 A | 8/2000 | Foreman et al. |
| 5,962,138 A | 10/1999 | Kolluri et al. | 6,110,188 A | 8/2000 | Narciso, Jr. |
| 5,965,720 A | 10/1999 | Gryaznov et al. | 6,110,483 A | 8/2000 | Whitbourne et al. |
| 5,968,091 A | 10/1999 | Pinchuk et al. | 6,113,629 A | 9/2000 | Ken |
| 5,968,092 A | 10/1999 | Buscemi et al. | 6,117,479 A | 9/2000 | Hogan et al. |
| 5,969,422 A | 10/1999 | Ting et al. | 6,117,979 A | 9/2000 | Hendriks et al. |
| 5,971,954 A | 10/1999 | Conway et al. | 6,120,477 A | 9/2000 | Campbell et al. |
| 5,972,027 A | 10/1999 | Johnson | 6,120,491 A | 9/2000 | Kohn et al. |
| 5,972,029 A | 10/1999 | Fuisz | 6,120,535 A | 9/2000 | McDonald et al. |
| 5,972,505 A | 10/1999 | Phillips et al. | 6,120,536 A | 9/2000 | Ding et al. |
| 5,976,155 A | 11/1999 | Foreman et al. | 6,120,788 A | 9/2000 | Barrows |
| 5,976,182 A | 11/1999 | Cox | 6,120,847 A | 9/2000 | Yang et al. |
| 5,980,564 A | 11/1999 | Stinson | 6,120,904 A | 9/2000 | Hostettler et al. |
| 5,980,928 A | 11/1999 | Terry | 6,121,027 A | 9/2000 | Clapper et al. |
| 5,980,972 A | 11/1999 | Ding | 6,123,712 A | 9/2000 | Di Caprio et al. |
| 5,981,568 A | 11/1999 | Kunz et al. | 6,125,523 A | 10/2000 | Brown et al. |
| 5,984,449 A | 11/1999 | Tajika et al. | 6,126,686 A | 10/2000 | Badylak et al. |
| 5,986,169 A | 11/1999 | Gjunter | 6,127,173 A | 10/2000 | Eckstein et al. |
| 5,997,468 A | 12/1999 | Wolff et al. | 6,129,761 A | 10/2000 | Hubbell |
| 5,997,517 A | 12/1999 | Whitbourne | 6,129,928 A | 10/2000 | Sarangapani et al. |
| 6,010,445 A | 1/2000 | Armini et al. | 6,132,809 A | 10/2000 | Hynes et al. |
| 6,010,530 A | 1/2000 | Goicoechea | 6,136,333 A | 10/2000 | Cohn et al. |
| 6,010,573 A | 1/2000 | Bowlin | 6,140,127 A | 10/2000 | Sprague |
| 6,011,125 A | 1/2000 | Lohmeijer et al. | 6,140,431 A | 10/2000 | Kinker et al. |
| 6,013,099 A | 1/2000 | Dinh et al. | 6,143,354 A | 11/2000 | Koulik et al. |
| 6,015,541 A | 1/2000 | Greff et al. | 6,143,370 A | 11/2000 | Panagiotou et al. |
| 6,019,789 A | 2/2000 | Dinh et al. | 6,149,574 A | 11/2000 | Trauthen et al. |
| 6,024,918 A | 2/2000 | Hendriks et al. | 6,150,630 A | 11/2000 | Perry et al. |
| 6,027,510 A | 2/2000 | Alt | 6,153,252 A | 11/2000 | Hossainy et al. |
| 6,027,526 A | 2/2000 | Limon et al. | 6,156,373 A | 12/2000 | Zhong et al. |
| 6,030,371 A | 2/2000 | Pursley | 6,159,227 A | 12/2000 | Di Caprio et al. |
| 6,033,582 A | 3/2000 | Lee et al. | 6,159,229 A | 12/2000 | Jendersee et al. |
| 6,033,719 A | 3/2000 | Keogh | 6,159,951 A | 12/2000 | Karpeisky et al. |
| 6,034,204 A | 3/2000 | Mohr et al. | 6,159,978 A | 12/2000 | Myers et al. |
| 6,042,606 A | 3/2000 | Frantzen | 6,160,084 A | 12/2000 | Langer et al. |
| 6,042,875 A | 3/2000 | Ding et al. | 6,165,212 A | 12/2000 | Dereume et al. |
| 6,045,899 A | 4/2000 | Wang et al. | 6,166,130 A | 12/2000 | Rhee et al. |
| 6,048,964 A | 4/2000 | Lee et al. | 6,168,617 B1 | 1/2001 | Blaeser et al. |
| 6,051,021 A | 4/2000 | Frid | 6,168,619 B1 | 1/2001 | Dinh et al. |
| 6,051,576 A | 4/2000 | Ashton et al. | 6,169,170 B1 | 1/2001 | Gryaznov et al. |
| 6,051,648 A | 4/2000 | Rhee et al. | 6,171,609 B1 | 1/2001 | Kunz |
| 6,054,553 A | 4/2000 | Groth et al. | 6,172,167 B1 | 1/2001 | Stapert et al. |
| 6,056,906 A | 5/2000 | Werneth et al. | 6,174,316 B1 | 1/2001 | Tuckey et al. |
| 6,056,993 A | 5/2000 | Leidner et al. | 6,174,330 B1 | 1/2001 | Stinson |
| 6,059,752 A | 5/2000 | Segal | 6,177,523 B1 | 1/2001 | Reich et al. |
| 6,059,810 A | 5/2000 | Brown et al. | 6,180,632 B1 | 1/2001 | Myers et al. |
| 6,060,451 A | 5/2000 | DiMaio et al. | 6,183,505 B1 | 2/2001 | Mohn, Jr. et al. |
| 6,060,518 A | 5/2000 | Kabanov et al. | 6,187,045 B1 | 2/2001 | Fehring et al. |
| 6,063,092 A | 5/2000 | Shin | 6,193,727 B1 | 2/2001 | Foreman et al. |
| 6,066,156 A | 5/2000 | Yan | 6,203,551 B1 | 3/2001 | Wu |
| 6,071,266 A | 6/2000 | Kelley | 6,209,621 B1 | 4/2001 | Treacy |
| 6,071,305 A | 6/2000 | Brown et al. | 6,210,715 B1 | 4/2001 | Starling et al. |
| 6,074,659 A | 6/2000 | Kunz et al. | 6,211,249 B1 | 4/2001 | Cohn et al. |
| 6,080,099 A | 6/2000 | Slater | 6,214,115 B1 | 4/2001 | Taylor et al. |
| 6,080,177 A | 6/2000 | Igaki et al. | 6,214,407 B1 | 4/2001 | Laube et al. |
| 6,080,190 A | 6/2000 | Schwartz | 6,214,901 B1 | 4/2001 | Chudzik et al. |
| 6,080,488 A | 6/2000 | Hostettler et al. | 6,217,586 B1 | 4/2001 | Mackenzie |
| 6,083,258 A | 7/2000 | Yadav | 6,217,721 B1 | 4/2001 | Xu et al. |
| 6,086,610 A | 7/2000 | Duerig et al. | 6,224,626 B1 | 5/2001 | Steinke |
| 6,090,330 A | 7/2000 | Gawa et al. | 6,224,675 B1 | 5/2001 | Prentice et al. |
| 6,093,199 A | 7/2000 | Brown et al. | 6,224,894 B1 | 5/2001 | Jamiolkowski et al. |
| 6,093,463 A | 7/2000 | Thakrar | 6,228,845 B1 | 5/2001 | Donovan et al. |
| 6,096,070 A | 8/2000 | Ragheb et al. | 6,231,590 B1 | 5/2001 | Slaikeu et al. |

| | | |
|---|---|---|
| 6,231,600 B1 | 5/2001 | Zhong |
| 6,240,616 B1 | 6/2001 | Yan |
| 6,242,041 B1 | 6/2001 | Katoot et al. |
| 6,245,076 B1 | 6/2001 | Yan |
| 6,245,099 B1 | 6/2001 | Edwin et al. |
| 6,245,103 B1 | 6/2001 | Stinson |
| 6,245,753 B1 | 6/2001 | Byun et al. |
| 6,245,760 B1 | 6/2001 | He et al. |
| 6,248,129 B1 | 6/2001 | Froix |
| 6,248,344 B1 | 6/2001 | Ylanen et al. |
| 6,251,135 B1 | 6/2001 | Stinson et al. |
| 6,251,136 B1 | 6/2001 | Guruwaiya et al. |
| 6,251,142 B1 | 6/2001 | Bernacca et al. |
| 6,253,443 B1 | 7/2001 | Johnson |
| 6,254,632 B1 | 7/2001 | Wu et al. |
| 6,258,099 B1 | 7/2001 | Mareiro et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,850 B1 | 8/2001 | Gambale |
| 6,273,913 B1 | 8/2001 | Wright et al. |
| 6,277,110 B1 | 8/2001 | Morales |
| 6,277,449 B1 | 8/2001 | Kolluri et al. |
| 6,279,368 B1 | 8/2001 | Escano et al. |
| 6,281,262 B1 | 8/2001 | Shikinami |
| 6,283,947 B1 | 9/2001 | Mirzaee |
| 6,283,949 B1 | 9/2001 | Roorda |
| 6,284,305 B1 | 9/2001 | Ding et al. |
| 6,284,333 B1 | 9/2001 | Wang et al. |
| 6,287,332 B1 | 9/2001 | Bolz et al. |
| 6,287,628 B1 | 9/2001 | Hossainy et al. |
| 6,290,721 B1 | 9/2001 | Heath |
| 6,293,966 B1 | 9/2001 | Frantzen |
| 6,294,836 B1 | 9/2001 | Paranjpe et al. |
| 6,296,603 B1 | 10/2001 | Turnlund et al. |
| 6,299,604 B1 | 10/2001 | Ragheb et al. |
| 6,303,901 B1 | 10/2001 | Perry et al. |
| 6,306,176 B1 | 10/2001 | Whitbourne |
| 6,312,459 B1 | 11/2001 | Huang et al. |
| 6,319,520 B1 | 11/2001 | Wuthrich et al. |
| 6,322,588 B1 | 11/2001 | Ogle et al. |
| 6,322,847 B1 | 11/2001 | Zhong et al. |
| 6,327,772 B1 | 12/2001 | Zadno-Azizi et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,099 B1 | 3/2002 | Gandikota et al. |
| 6,364,903 B2 | 4/2002 | Tseng et al. |
| 6,375,458 B1 | 4/2002 | Moorleghem et al. |
| 6,375,826 B1 | 4/2002 | Wang et al. |
| 6,379,379 B1 | 4/2002 | Wang |
| 6,379,381 B1 | 4/2002 | Hossainy et al. |
| 6,387,118 B1 | 5/2002 | Hanson |
| 6,387,121 B1 | 5/2002 | Alt |
| 6,387,379 B1 | 5/2002 | Goldberg et al. |
| 6,388,043 B1 | 5/2002 | Langer et al. |
| 6,395,325 B1 | 5/2002 | Hedge et al. |
| 6,395,326 B1 | 5/2002 | Castro et al. |
| 6,406,738 B1 | 6/2002 | Hogan et al. |
| 6,409,761 B1 | 6/2002 | Jang |
| 6,413,272 B1 | 7/2002 | Igaki |
| 6,419,692 B1 | 7/2002 | Yang et al. |
| 6,420,189 B1 | 7/2002 | Lopatin |
| 6,423,092 B2 | 7/2002 | Datta et al. |
| 6,436,816 B1 | 8/2002 | Lee et al. |
| 6,444,567 B1 | 9/2002 | Besser et al. |
| 6,447,835 B1 | 9/2002 | Wang et al. |
| 6,451,373 B1 | 9/2002 | Hossainy et al. |
| 6,454,738 B1 | 9/2002 | Tran et al. |
| 6,455,424 B1 | 9/2002 | McTeer et al. |
| 6,461,632 B1 | 10/2002 | Gogolewski |
| 6,462,284 B1 | 10/2002 | Hashimoto |
| 6,464,720 B2 | 10/2002 | Boatman et al. |
| 6,468,906 B1 | 10/2002 | Chan et al. |
| 6,479,565 B1 | 11/2002 | Stanley |
| 6,481,262 B2 | 11/2002 | Ching et al. |
| 6,482,834 B2 | 11/2002 | Spada et al. |
| 6,485,512 B1 | 11/2002 | Cheng |
| 6,488,701 B1 | 12/2002 | Nolting et al. |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,888 B1 | 2/2003 | Weber |
| 6,517,889 B1 | 2/2003 | Jayaraman |
| 6,521,284 B1 | 2/2003 | Parsons et al. |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,537,589 B1 | 3/2003 | Chae et al. |
| 6,539,607 B1 | 4/2003 | Fehring et al. |
| 6,540,776 B2 | 4/2003 | Sanders Millare et al. |
| 6,540,777 B2 | 4/2003 | Stenzel |
| 6,544,223 B1 | 4/2003 | Kokish |
| 6,544,543 B1 | 4/2003 | Mandrusov et al. |
| 6,544,582 B1 | 4/2003 | Yoe |
| 6,554,758 B2 | 4/2003 | Turnlund et al. |
| 6,554,854 B1 | 4/2003 | Flanagan |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,599 B1 | 5/2003 | Hong et al. |
| 6,565,659 B1 | 5/2003 | Pacetti et al. |
| 6,569,191 B1 | 5/2003 | Hogan |
| 6,569,193 B1 | 5/2003 | Cox et al. |
| 6,572,644 B1 | 6/2003 | Moein |
| 6,572,672 B2 | 6/2003 | Yadav et al. |
| 6,574,851 B1 | 6/2003 | Mirizzi |
| 6,582,417 B1 | 6/2003 | Ledesma et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,592,614 B2 | 7/2003 | Lenker et al. |
| 6,592,617 B2 | 7/2003 | Thompson |
| 6,596,296 B1 | 7/2003 | Nelson et al. |
| 6,605,114 B1 | 8/2003 | Yan et al. |
| 6,605,154 B1 | 8/2003 | Villareal |
| 6,605,874 B2 | 8/2003 | Leu et al. |
| 6,610,087 B1 | 8/2003 | Zarbatany et al. |
| 6,613,072 B2 | 9/2003 | Lau et al. |
| 6,616,765 B1 | 9/2003 | Castro et al. |
| 6,623,448 B2 | 9/2003 | Slater |
| 6,625,486 B2 | 9/2003 | Lundkvist et al. |
| 6,626,939 B1 | 9/2003 | Burnside et al. |
| 6,635,269 B1 | 10/2003 | Jennissen |
| 6,635,964 B2 | 10/2003 | Maex et al. |
| 6,645,135 B1 | 11/2003 | Bhat |
| 6,645,195 B1 | 11/2003 | Bhat et al. |

| | | | | | |
|---|---|---|---|---|---|
| 6,645,243 B2 | 11/2003 | Vallana et al. | 2002/0005206 A1 | 1/2002 | Falotico et al. |
| 6,645,547 B1 | 11/2003 | Shekalim et al. | 2002/0007213 A1 | 1/2002 | Falotico et al. |
| 6,656,162 B2 | 12/2003 | Santini, Jr. et al. | 2002/0007214 A1 | 1/2002 | Falotico |
| 6,656,216 B1 | 12/2003 | Hossainy et al. | 2002/0007215 A1 | 1/2002 | Falotico et al. |
| 6,656,506 B1 | 12/2003 | Wu et al. | 2002/0009604 A1 | 1/2002 | Zamora et al. |
| 6,660,034 B1 | 12/2003 | Mandrusov et al. | 2002/0016625 A1 | 2/2002 | Falotico et al. |
| 6,663,662 B2 | 12/2003 | Pacetti et al. | 2002/0032414 A1 | 3/2002 | Ragheb et al. |
| 6,663,880 B1 | 12/2003 | Roorda et al. | 2002/0032434 A1 | 3/2002 | Chudzik et al. |
| 6,664,187 B1 | 12/2003 | Ngo et al. | 2002/0051730 A1 | 5/2002 | Bodnar et al. |
| 6,664,335 B2 | 12/2003 | Krishnan | 2002/0062148 A1 | 5/2002 | Hart |
| 6,666,214 B2 | 12/2003 | Canham | 2002/0065553 A1 | 5/2002 | Weber |
| 6,666,880 B1 | 12/2003 | Chiu et al. | 2002/0071822 A1 | 6/2002 | Uhrich |
| 6,667,049 B2 | 12/2003 | Janas et al. | 2002/0077693 A1 | 6/2002 | Barclay et al. |
| 6,669,723 B2 | 12/2003 | Killion et al. | 2002/0082679 A1 | 6/2002 | Sirhan et al. |
| 6,669,980 B2 | 12/2003 | Hansen | 2002/0087123 A1 | 7/2002 | Hossainy et al. |
| 6,673,154 B1 | 1/2004 | Pacetti et al. | 2002/0091433 A1 | 7/2002 | Ding et al. |
| 6,673,385 B1 | 1/2004 | Ding et al. | 2002/0094440 A1 | 7/2002 | Llanos et al. |
| 6,676,697 B1 | 1/2004 | Richter | 2002/0111590 A1 | 8/2002 | Davila et al. |
| 6,676,700 B1 | 1/2004 | Jacobs et al. | 2002/0116050 A1 | 8/2002 | Kocur |
| 6,679,980 B1 | 1/2004 | Andreacchi | 2002/0120326 A1 | 8/2002 | Michal |
| 6,689,099 B2 | 2/2004 | Mirzaee | 2002/0138133 A1 | 9/2002 | Lenz et al. |
| 6,689,375 B1 | 2/2004 | Wahlig et al. | 2002/0142039 A1 | 10/2002 | Claude |
| 6,695,920 B1 | 2/2004 | Pacetti et al. | 2002/0155212 A1 | 10/2002 | Hossainy |
| 6,699,281 B2 | 3/2004 | Vallana et al. | 2002/0161114 A1 | 10/2002 | Gunatillake et al. |
| 6,703,307 B2 | 3/2004 | Lopatin et al. | 2002/0165608 A1 | 11/2002 | Llanos et al. |
| 6,706,013 B1 | 3/2004 | Bhat et al. | 2002/0176849 A1 | 11/2002 | Slepian |
| 6,706,273 B1 | 3/2004 | Roessler | 2002/0183581 A1 | 12/2002 | Yoe et al. |
| 6,709,379 B1 | 3/2004 | Brandau et al. | 2002/0187632 A1 | 12/2002 | Marsh |
| 6,709,514 B1 | 3/2004 | Hossainy | 2002/0188037 A1 | 12/2002 | Chudzik et al. |
| 6,712,845 B2 | 3/2004 | Hossainy | 2002/0188277 A1 | 12/2002 | Roorda et al. |
| 6,713,119 B2 | 3/2004 | Hossainy et al. | 2003/0003221 A1 | 1/2003 | Zhong et al. |
| 6,716,444 B1 | 4/2004 | Castro et al. | 2003/0004141 A1 | 1/2003 | Brown |
| 6,719,934 B2 | 4/2004 | Stinson | 2003/0028243 A1 | 2/2003 | Bates et al. |
| 6,719,989 B1 | 4/2004 | Matsushima et al. | 2003/0028244 A1 | 2/2003 | Bates et al. |
| 6,720,402 B2 | 4/2004 | Langer et al. | 2003/0031780 A1 | 2/2003 | Chudzik et al. |
| 6,723,120 B2 | 4/2004 | Yan | 2003/0032767 A1 | 2/2003 | Tada et al. |
| 6,733,768 B2 | 5/2004 | Hossainy et al. | 2003/0033001 A1 | 2/2003 | Igaki |
| 6,740,040 B1 | 5/2004 | Mandrusov et al. | 2003/0036794 A1 | 2/2003 | Ragheb et al. |
| 6,743,462 B1 | 6/2004 | Pacetti | 2003/0039689 A1 | 2/2003 | Chen et al. |
| 6,746,773 B2 | 6/2004 | Llanos et al. | 2003/0040712 A1 | 2/2003 | Ray et al. |
| 6,749,626 B1 | 6/2004 | Bhat et al. | 2003/0040790 A1 | 2/2003 | Furst |
| 6,752,826 B2 | 6/2004 | Holloway et al. | 2003/0054090 A1 | 3/2003 | Hansen |
| 6,753,007 B2 | 6/2004 | Haggard et al. | 2003/0055482 A1 | 3/2003 | Schwager et al. |
| 6,753,071 B1 | 6/2004 | Pacetti et al. | 2003/0059520 A1 | 3/2003 | Chen et al. |
| 6,758,859 B1 | 7/2004 | Dang et al. | 2003/0060877 A1 | 3/2003 | Falotico et al. |
| 6,759,054 B2 | 7/2004 | Chen et al. | 2003/0065377 A1 | 4/2003 | Davila et al. |
| 6,764,505 B1 | 7/2004 | Hossainy et al. | 2003/0072868 A1 | 4/2003 | Harish et al. |
| 6,774,278 B1 | 8/2004 | Ragheb et al. | 2003/0073961 A1 | 4/2003 | Happ |
| 6,776,792 B1 | 8/2004 | Yan et al. | 2003/0083646 A1 | 5/2003 | Sirhan et al. |
| 6,783,793 B1 | 8/2004 | Hossainy et al. | 2003/0083739 A1 | 5/2003 | Cafferata |
| 6,818,063 B1 | 11/2004 | Kerrigan | 2003/0088307 A1 | 5/2003 | Shulze et al. |
| 6,846,323 B2 | 1/2005 | Yip et al. | 2003/0093107 A1 | 5/2003 | Parsonage et al. |
| 6,860,946 B2 | 3/2005 | Hossainy et al. | 2003/0097088 A1 | 5/2003 | Pacetti |
| 6,861,088 B2 | 3/2005 | Weber et al. | 2003/0097173 A1 | 5/2003 | Dutta |
| 6,865,810 B2 | 3/2005 | Stinson | 2003/0099712 A1 | 5/2003 | Jayaraman |
| 6,869,443 B2 | 3/2005 | Buscemi et al. | 2003/0100865 A1 | 5/2003 | Santini, Jr. et al. |
| 6,878,160 B2 | 4/2005 | Gilligan et al. | 2003/0105518 A1 | 6/2003 | Dutta |
| 6,887,270 B2 | 5/2005 | Miller et al. | 2003/0105530 A1 | 6/2003 | Pirhonen |
| 6,887,485 B2 | 5/2005 | Fitzhugh et al. | 2003/0113439 A1 | 6/2003 | Pacetti et al. |
| 6,890,546 B2 | 5/2005 | Mollison et al. | 2003/0113445 A1 | 6/2003 | Martin |
| 6,899,731 B2 | 5/2005 | Li et al. | 2003/0138487 A1 | 7/2003 | Hogan et al. |
| 2001/0001806 A1 | 5/2001 | Turnlund et al. | 2003/0150380 A1 | 8/2003 | Yoe |
| 2001/0007083 A1 | 7/2001 | Roorda | 2003/0157241 A1 | 8/2003 | Hossainy et al. |
| 2001/0014717 A1 | 8/2001 | Hossainy et al. | 2003/0158517 A1 | 8/2003 | Kokish |
| 2001/0016753 A1 | 8/2001 | Caprio et al. | 2003/0171053 A1 | 9/2003 | Sanders |
| 2001/0020011 A1 | 9/2001 | Mathiowitz et al. | 2003/0185964 A1 | 10/2003 | Weber et al. |
| 2001/0029351 A1 | 10/2001 | Falotico et al. | 2003/0187495 A1 | 10/2003 | Cully et al. |
| 2001/0037145 A1 | 11/2001 | Guruwaiya et al. | 2003/0190406 A1 | 10/2003 | Hossainy et al. |
| 2001/0044652 A1 | 11/2001 | Moore | 2003/0203617 A1 | 10/2003 | Lane et al. |
| 2001/0051608 A1 | 12/2001 | Mathiowitz et al. | 2003/0207020 A1 | 11/2003 | Villareal |
| 2002/0002399 A1 | 1/2002 | Huxel et al. | 2003/0208259 A1 | 11/2003 | Penhasi |
| 2002/0004060 A1 | 1/2002 | Heublein et al. | 2003/0209835 A1 | 11/2003 | Chun et al. |
| 2002/0004101 A1 | 1/2002 | Ding et al. | 2003/0211230 A1 | 11/2003 | Pacetti et al. |

| | | | | | | |
|---|---|---|---|---|---|---|
| 2003/0226833 | A1 | 12/2003 | Shapovalov et al. | EP | 0 623 354 | 11/1994 |
| 2003/0236565 | A1 | 12/2003 | DiMatteo et al. | EP | 0 627 226 | 12/1994 |
| 2004/0018296 | A1 | 1/2004 | Castro et al. | EP | 0 649 637 | 4/1995 |
| 2004/0029952 | A1 | 2/2004 | Chen et al. | EP | 0 665 023 | 8/1995 |
| 2004/0047978 | A1 | 3/2004 | Hossainy et al. | EP | 0 701 802 | 3/1996 |
| 2004/0047980 | A1 | 3/2004 | Pacetti et al. | EP | 0 701 803 | 3/1996 |
| 2004/0052858 | A1 | 3/2004 | Wu et al. | EP | 0 709 068 | 5/1996 |
| 2004/0052859 | A1 | 3/2004 | Wu et al. | EP | 0 716 836 | 6/1996 |
| 2004/0054104 | A1 | 3/2004 | Pacetti | EP | 0 732 087 | 9/1996 |
| 2004/0060508 | A1 | 4/2004 | Pacetti et al. | EP | 0 832 618 | 9/1996 |
| 2004/0062853 | A1 | 4/2004 | Pacetti et al. | EP | 0 756 853 | 2/1997 |
| 2004/0063805 | A1 | 4/2004 | Pacetti et al. | EP | 0 809 999 | 12/1997 |
| 2004/0071861 | A1 | 4/2004 | Mandrusov et al. | EP | 0 832 655 | 4/1998 |
| 2004/0072922 | A1 | 4/2004 | Hossainy et al. | EP | 0 834 293 | 4/1998 |
| 2004/0073298 | A1 | 4/2004 | Hossainy | EP | 0 850 604 | 7/1998 |
| 2004/0086542 | A1 | 5/2004 | Hossainy et al. | EP | 0 850 651 | 7/1998 |
| 2004/0086550 | A1 | 5/2004 | Roorda et al. | EP | 0 879 595 | 11/1998 |
| 2004/0093077 | A1 | 5/2004 | White et al. | EP | 0 910 584 | 4/1999 |
| 2004/0096504 | A1 | 5/2004 | Michal | EP | 0 923 953 | 6/1999 |
| 2004/0098095 | A1 | 5/2004 | Burnside et al. | EP | 0 953 320 | 11/1999 |
| 2004/0098117 | A1 | 5/2004 | Hossainy et al. | EP | 0 972 498 | 1/2000 |
| 2004/0111149 | A1 | 6/2004 | Stinson | EP | 0 974 315 | 1/2000 |
| 2004/0127970 | A1 | 7/2004 | Saunders | EP | 0970711 | 1/2000 |
| 2004/0142015 | A1 | 7/2004 | Hossainy et al. | EP | 0 982 041 | 3/2000 |
| 2004/0143317 | A1 | 7/2004 | Stinson et al. | EP | 1 023 879 | 8/2000 |
| 2004/0167610 | A1 | 8/2004 | Fleming, III | EP | 1 034 752 | 9/2000 |
| 2004/0213893 | A1 | 10/2004 | Boulais | EP | 1 075 838 | 2/2001 |
| 2004/0236417 | A1 | 11/2004 | Yan et al. | EP | 1 103 234 | 5/2001 |
| 2005/0038497 | A1 | 2/2005 | Neuendorf et al. | EP | 1 192 957 | 4/2002 |
| 2005/0043786 | A1 | 2/2005 | Chu et al. | EP | 1 273 314 | 1/2003 |
| 2005/0049694 | A1 | 3/2005 | Neary | EP | 0 869 847 | 3/2003 |
| 2005/0054774 | A1 | 3/2005 | Kangas | EP | 0 941 072 | 1/2004 |
| 2005/0055044 | A1 | 3/2005 | Kangas | FR | 2 753 907 | 4/1998 |
| 2005/0060020 | A1 | 3/2005 | Jenson | GB | 2 247 696 | 3/1992 |
| 2005/0064088 | A1 | 3/2005 | Fredrickson | GB | 2 316 086 | 1/2000 |
| 2005/0065501 | A1 | 3/2005 | Wallace | GB | 2 316 342 | 1/2000 |
| 2005/0065545 | A1 | 3/2005 | Wallace | GB | 2 333 975 | 1/2000 |
| 2005/0065593 | A1 | 3/2005 | Chu et al. | GB | 2 336 551 | 1/2000 |
| 2005/0074406 | A1 | 4/2005 | Couvillon, Jr. et al. | GB | 2 356 586 | 5/2001 |
| 2005/0074545 | A1 | 4/2005 | Thomas | GB | 2 356 587 | 5/2001 |
| 2005/0079274 | A1 | 4/2005 | Palasis et al. | GB | 2 333 474 | 6/2001 |
| | | | | GB | 2 334 685 | 6/2001 |

FOREIGN PATENT DOCUMENTS

| | | |
|---|---|---|
| CA | 2 007 648 | 4/1991 |
| CA | 1 322 628 | 10/1993 |
| CA | 1 336 319 | 7/1995 |
| CA | 1 338 303 | 5/1996 |
| DE | 042 24 401 | 1/1994 |
| DE | 044 07 079 | 9/1994 |
| DE | 197 31 021 | 1/1999 |
| DE | 19916086 | 10/1999 |
| DE | 198 56 983 | 12/1999 |
| EP | 0 108 171 | 5/1984 |
| EP | 0 144 534 | 6/1985 |
| EP | 0 301 856 | 2/1989 |
| EP | 0 380 668 | 4/1989 |
| EP | 0 351 314 | 1/1990 |
| EP | 0 364 787 | 4/1990 |
| EP | 0 396 429 | 11/1990 |
| EP | 0 397 500 | 11/1990 |
| EP | 0 464 755 | 1/1992 |
| EP | 0 493 788 | 7/1992 |
| EP | 0 526 606 | 9/1992 |
| EP | 0 514 406 | 11/1992 |
| EP | 0 517 075 | 12/1992 |
| EP | 0 540 290 | 5/1993 |
| EP | 0 553 960 | 8/1993 |
| EP | 0 554 082 | 8/1993 |
| EP | 0 565 251 | 10/1993 |
| EP | 0 578 998 | 1/1994 |
| EP | 0 604 022 | 6/1994 |
| EP | 0 621 017 | 10/1994 |
| GB | 2 356 585 | 7/2001 |
| GB | 2 374 302 | 8/2001 |
| GB | 2 370 243 | 6/2002 |
| GB | 2 384 199 | 7/2003 |
| JP | SHO49-48336 | 12/1974 |
| JP | SHO54-18310 | 7/1979 |
| JP | SHO60-28504 | 7/1985 |
| JP | 21199867 | 5/1994 |
| JP | HEI8-33718 | 2/1996 |
| JP | HEI10-151190 | 6/1998 |
| JP | 2919971 B2 | 7/1999 |
| JP | 2001-190687 | 7/2001 |
| SU | 0872531 | 10/1981 |
| SU | 0876663 | 10/1981 |
| SU | 0905228 | 2/1982 |
| SU | 0790725 | 2/1983 |
| SU | 1016314 | 5/1983 |
| SU | 0811750 | 9/1983 |
| SU | 1293518 | 2/1987 |
| SU | 1477423 | 5/1989 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/11176 | 8/1991 |
| WO | WO 91/12846 | 9/1991 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/09760 | 5/1994 |

| | | |
|---|---|---|
| WO | WO 94/21196 | 9/1994 |
| WO | WO 95/10989 | 4/1995 |
| WO | WO 95/11817 | 5/1995 |
| WO | WO 95/24929 | 9/1995 |
| WO | WO 95/29647 | 11/1995 |
| WO | WO 95/33422 | 12/1995 |
| WO | WO 96/28115 | 9/1996 |
| WO | WO 96/35516 | 11/1996 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/04415 | 2/1998 |
| WO | WO 98/07390 | 2/1998 |
| WO | WO 98/08463 | 3/1998 |
| WO | WO 98/17331 | 4/1998 |
| WO | WO 98/20863 | 5/1998 |
| WO | WO 98/23228 | 6/1998 |
| WO | WO 98/32398 | 7/1998 |
| WO | WO 98/36784 | 8/1998 |
| WO | WO 9836784 A1 * | 8/1998 |
| WO | WO 99/01118 | 1/1999 |
| WO | WO 99/03515 | 1/1999 |
| WO | WO 99/16386 | 4/1999 |
| WO | WO 9916386 A1 * | 4/1999 |
| WO | WO 99/38546 | 8/1999 |
| WO | WO 99/42147 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17459 | 3/2001 |
| WO | WO 01/17577 | 3/2001 |
| WO | WO 01/43727 | 6/2001 |
| WO | WO 01/45763 | 6/2001 |
| WO | WO 01/49338 | 7/2001 |
| WO | WO 01/51027 | 7/2001 |
| WO | WO 01/52772 | 7/2001 |
| WO | WO 01/57144 | 8/2001 |
| WO | WO 01/74414 | 10/2001 |
| WO | WO 01/91918 | 12/2001 |
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

Fischell et al., *Low-Dose, β-Particle Emission from 'Stent' Wire Results in Complete, Localized Inhibition of Smooth Muscle Cell Proliferation*, Circulation, vol. 90(6):2956-2963, Dec. 1994.
Hehrlein et al., *Low-Dose Radioactive Endovascular Stents Prevent Smooth Muscle Cell Proliferation and Neointimal Hyperplasia in Rabbits*, Circulation, vol. 92(6):1570-1575, Sep. 15, 1995.
Liermann et al., *Prophylactic Endovascular Radiotherapy to Prevent Intimal Hyperplasia after Stent Implantation in Femoropopliteal Arteries*, CardioVascular and Interventional Radiology 17:12-16, 1994.
Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A 15(6):2875-2879 (Nov./Dec. 1997).
Malik et al., *Overview of Plasma Source Ion Implantation Research at University of Wisconsin-Madison*, J. Vac. Sci. Technol. B 12(2):843-849 (Mar./Apr. 1994).
Malik et al., *Sheath Dynamics and Dose Analysis for Planar Targets in Plasma Source Ion Implantation*, Plasma Sources Sci. Technol. 2:81-85 (1993).
Matsumaru et al., *Embolic Materials for Endovascular Treatment of Cerebral Lesions*, J. Biomater. Sci. Polymer Edn. 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6):2490-2498 (1985).
Miyazawa et al., *Effects of Pemirolast and Tranilast on Intimal Thickening After Arterial Injury in the Rat*, J. Cardiovasc. Pharmacol. 30(2):157-162 (1997).
Ohsawa et al., *Preventive Effects of an Antiallergic Drug, Pemirolast Potassium, on Restenosis After Percutaneous Transluminal Coronary Angioplasty*, Am. Heart J. 136(6):1081-1087 (Dec. 1998).
Scheuer et al., *Model of Plasma Source Ion Implantation in Planar, Cylindrical, and Spherical Geometries*, J. Appl. Phys. 67(3):1241-1245 (Feb. 1990).
Serruys et al., *I Like the Candy, I Hate the Wrapper, the $^{32}P$ Radioactive Stent*, Circulation 101:3-7 (Jan. 2000).
Shamim et al., *Measurement of Electron Emission Due to Energetic Ion Bombardment in Plasma Source Ion Implantation*, J. Appl. Phys. 70(9):4756-4759 (Nov. 1991).
Shamim et al., *Measurements of Spatial and Temporal Sheath Evolution for Spherical and Cylindrical Geometrics in Plasma Source Ion Implantation*, J. Appl. Phys. 69(5):2904-2908 (Mar. 1991).
Shigeno, *Prevention of Cerebrovascular Spasm by Bosentan, Novel Endothelin Receptor*, Chem. Abstracts 125:212307 (1996).
van der Giessen et al., "Edge Effect" of $^{32}P$ Radioactive Stents is Caused by the Combination of Chronic Stent Injury and Radioactive Dose Falloff, Circ. 104:2236-2241 (Oct. 30, 2001).
Wiesendanger et al., *Contributions Of Scanning Probe Microscopy And Spectroscopy To The Investigation And Fabrication Of Nanometer-Scale Structures*, J. Vac. Sci. Technol. B, 12(2):515-529 (Mar./Apr. 1994).
U.S. Appl. No. 10/255,913, filed Sep. 26, 2002, Tang et al.
U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10,409,410, filed Apr. 7, 2003, Pacetti.
U.S. Appl. No. 10,439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905, filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/747,996, filed Dec. 29, 2003, Chen et al.
U.S. Appl. No. 10/750,139, filed Dec. 30, 2003, DesNoyer et al.

U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
U.S. Appl. No. 10/833,902, filed Apr. 27, 2004, Chen et al.
U.S. Appl. No. 10/835,229, filed Apr. 28, 2004, Prabhu et al.
U.S. Appl. No. 10/835,656, filed Apr. 30, 2004, Tang et al.
U.S. Appl. No. 10/851,411, filed May 20, 2004, Chen.
U.S. Appl. No. 10/855,294, filed May 26, 2004, Pacetti et al.
U.S. Appl. No. 10/877,527, filed Jun. 24, 2004, Yan et al.
Angioplasty.org., *Balloons and Stents*, http://www.ptca.org/devices04.html, printed Oct. 15, 2004, 2 pages.
Anonymous, *Bioabsorbable stent mounted on a catheter having optical coherence tomography capabilities*, Research Disclosure, pp. 1159-1162 (Sep. 2004).
Anonymous, *Capillary Action*, http://www.ndt-ed.org/EducationResources/CommunityCollege/PenetrantTest/Introduction/Keywords/pt1.htm, printed Aug. 12, 2005, 1 page.
Anonymous, *Capillary Force Lithography (CFL)*, Nano Processing and Organic Devices Lab, 2 pages, no date.
Anonymous, *Capillary Rise of Liquid in Differenct Vanes Under Variable Residual Acceleration*, http://www.zarm.uni-bremen.de/2forschung/grenzph/isoterm/cap_rise/kapst_en.htm, ZARM—University of Bremen, printed Jun. 25, 2003, 2 pages.
Anonymous, *Cardiologists Draw—Up The Dream Stent*, Clinica 710, pp. 15 (Jun. 17, 1996), http://www.dialogweb.com/cgi/document?req=1061848202959, printed Aug. 25, 2003, 2 pages.
Anonymous, *Coating Techniques, Air Knife Coating*, http://www.ferron-magnetic.co.uk/coatings/airknife.htm, printed Jul. 1, 2003, 1 page.
Anonymous, *Coating Techniques, Gap Coating (Knife Over Roll, etc.)*, http://www.ferron-magentic.co.uk/coatings/knife.htm, printed Jul. 1, 2003, 1 page.
Anonymous, *Coating Techniques, Gravure Coating*, http://www.ferron-magnetic.co.uk/coatings/gravure.htm, printed Jul. 1, 2003, 2 pages.
Anonymous, *Coating Techniques, Reverse Roll Coating*, http://www.ferron-magnetic.co.uk/coatings/revroll.htm, printed Jul. 1, 2003, 22 pages.
Anonymous, *Heparin-coated stents cut complications By 30%*, Clinica 732, pp. 17 (Nov. 18, 1996), http://www.dialogweb.com/cgi/document?reg=1061847871753, printed Aug. 25, 2003, 2 pages.
Anonymous, *Liquid Gravity Motor*, http://w ww.drspark86.com/idea001.html, printed Jun. 24, 2003, 2 pages, no date.
Anonymous, *Porosimetry—Why characterize the porosity?* 42 pages, no date.
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting Continues to Dominate Cardiology*, http://www.dialogweb.com/cgi/document?reg=1061848017752, Clinica vol. 720, pp. 22 (Sep. 2, 1996), printed Aug. 25, 2003, 2 pages.
Anonymous, *Surface Energy (Surface Wetting Capability)*, http://www.ndt-ed.org/EducationResources/CommunityCollege/PenetrantTest/PTMaterials/surfaceenergy.htm, printed Apr. 6, 2004, 3 pages, no date.
Anonymous, *The 14th International Young Physicists Tournament, The winning report*, Research Center for Quantum Information, Slovak Academy of Sciences, 5 pages, no date.
Anonymous, *The Wicking Well System*, http://www.decorative.com/wicking.html, printed Jun. 24, 2003, 1 page.
Anonymous, *Typical Parylene Properties*, 3 pages, no date.
Anonymous, *Viscosity*, Commonwealth of Australia, 7 pages, no date.
Ansari, *End-to-End Tubal Anastomosis Using an Absorbable Stent*, Fertility and Sterility, vol. 32, No. 2, pp. 197-201 (Aug. 1979).
Ansari, *Tubal Reanastomosis Using Absorbable Stent*, International Journal of Fertility, vol. 23, No. 4, pp. 242-243 (1978).
Aoyagi et al., *Preparation of cross-linked aliphatic polyester and application to thermo-responsive material*, Journal of Controlled Release 32, pp. 87-96 (1994).
Barbucci et al., *Coating of commercially available materials with a new heparinizable Material*, Journal of Biomedical Materials Research, vol. 25, pp. 1259-1274 (1991).

Beach et al., *Xylylene Polymers*, Encyclopedia of Polymer Science and Engineering, vol. 17, 2nd Edition, pp. 990-1025 (1989).
Boston Scientific, *Express ² ™ Coronary Stent System*, http://www.bostonscientific.com/med_specialty/deviceDetail.jsp?task=tskBasicDevice.jsp&sectionId=4&reIId=2,74,75,76&deviceId=11001&uniqueId=MPDB1180&clickType=endeca, printed Aug. 8, 2005, 1 page.
Bull, *Parylene Coating for Medical Applications*, Medical Product Manufacturing News, 2 pages (Mar. 1993).
Casper et al., *Fiber-Reinforced Absorbable Composite for Orthopedic Surgery*, Polymeric Materials Science and Engineering, vol. 53, pp. 497-501(1985).
Charlson et al., *Temperature Selective Deposition of Parylene-C*, IEEE Transactions of Biomedical Engineering, vol. 39, No. 2, pp. 202-206 (Feb. 1992).
Chen et al., *The Kinetics of Wicking of Liquid Droplets into Yarns*, submitted to the Textile Research Journal, pp. 1-30 (Apr. 2001).
Chung et al., *Inner core segment design for drug delivery control of thermo-responsive polymeric micelles*, Journal of Controlled Release, vol. 65, pp. 93-103 (2000).
Crowe et al., *Absorption and Intestinal Metabolism of SDZ-RAD and Rapamycin in Rats*, Drug Metabolism and Disposition, vol. 27 No. 5, pp. 627-632 (1999).
De Scheerder et al., *Biocompatibility of polymer-coated oversized metallic stents implanted in normal porcine coronary arteries*, Atherosclerosis, vol. 114, pp. 105-114 (1995).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).
Dev et al., Kinetics of Drug Delivery to the Arterial Wall Via Polyurethane-Coated Removable Nitinol Stent: Comparative Study of Two Drugs, Catheterization and Cardiovascular Diagnosis, vol. 34, pp. 272-278 (1995).
Devanathan et al., *Polymeric Conformal Coatings for Implantable Electronic Devices*, IEEE Transactions on Biomedical Engineering, vol. BME-27, No. 11, pp. 671-675 (1980).
Dichek et al., *Seeding of Intravascular Stents with Genetically Engineered Endothelial Cells*, Circulation, vol. 80, No. 5, pp. 1347-1353 (Nov. 1989).
Dreyer et al., *Critical Velocities in Open Capillary Flows*, pp. 604-609, no date.
Duerig et al., *A comparison of balloon-and self-expanding stents*, Min. Invas. Ther. & Allied Technol., vol. 11, No. 4, pp. 173-178 (2002).
Dutkiewicz, *Some Advances in Nonwoven Structures for Absorbency, Comfort and Aesthetics*, AUTEX Reserch Journal, vol. 2, No. 3, pp. 153-165 (Sep. 2002).
EFD, *780S Series Spray Valves VALVEMATE™ 7040 Controller Operating Manual*, 24 pages (2002).
Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).
Elbert et al., *Conjugate Addition Reactions Combined with Free-Radical Cross-Linking for the Design of Materials for Tissue Engineering*, Biomacromolecules, vol. 2, pp. 430-441 (2001).
Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).
Eskin et al., *Tissue Cultured Cells: Potential Blood Compatible Linings for Cardiovascular Prostheses*, Polymer Science and Technology, vol. 14, pp. 143-161, no date.
Fischell et al., *The Bx VELOCITY™ STENT*, 5 pages, Biocompatibles Ltd. (2001).
Gengenbach et al., *Evolution of the Surface Composition and Topography of Perflurinated Polymers Following Ammonia-Plasma Treatment*, Plasma Surface Modifications of Polymers, pp. 123-146 (1994).
Gercken et al., *Results of the Jostent Coronary Stent Graft Implantation in Various Clinical Settings: Procedrual and Follow-Up Results*, vol. 56, No. 3, pp. 353-360 (2002).
Gölander et al., *RF-Plasma-Modified Polystyrene Surfaces for Studying Complement Activation*, J. Biomater. Sci. Plymer Edn., vol. 4, No. 1 pp. 25-30 (1992).
Guidant, *ACS RX Multi-Link™ Coronary Stent System*, 6 pages, no date.
Guidant, *Guidant Multi-Link Vision OTW Coronary Stent System*, 2 pages, no date.
Hahn et al., *Biocompatibility of Glow-Discharge-Polmerized Films and Vacuum-Deposited Parylene*, Journal of Applied Polymer Science: Applied Polymer Symposium 38, 55-64 (1984).
Hahn et al., *Glow Discharge Polymers as Coatings for Implanted Devices*, John M. Dalton Research Center, University of Missouri-Columbia and the Graduate Center for Materials Research, pp. 109-113 (1981).
He et al., *Assessment of Tissue Blood Flow Following Small Artery Welding with an Intraluminal Dissolvable Stent*, Microsurgery, vol. 19, No. 3, pp. 148-152 (1999).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol., vol. 3, pp. 197-199 (1998).
Hollahan et al. *Attachment of Amino Groups to Polymer Surfaces by Radiofrequency Plasmas*, Journal of Applied Polymer Science, vol. 13, pp. 807-816 (1969).
Huang et al., *Biodegradable Polymers Derived from Aminoacids*, Macromol. Symp. 144, 7-32 (1999).
Impulse Jetting, *About Us*, http://www.impulsejetting.com/about.html, printed Dec. 18, 2000, 1 page.
Impulse Jetting, *Our Technology*, http://www.impulsejetting.com/tech1.html, printed Dec. 18, 2000, 1 page.
Inagaki et al., *Hydrophilic Surface Modification of Polyethylene by No-Plasma Treatment*, Adhesion Sci. Technol., vol. 4, No. 2, pp. 99-107 (1990).
Inoue et al., *An AB block copolymer of oligo(methyl methacrylate) and poly(acrylic acid) for micellar delivery of hydrophobic drugs*, Journal of Controlled Release, vol. 51, pp. 221-229 (1998).
International Search Report and Written Opinion of PCT Application No. PCT/US2004/026137 filed Aug. 11, 2004 (Jan. 31, 2005).
Itabashi et al., *Electroless Deposited CoWB for Copper Diffusion Barrier Metal*, International Interconnect Technology Conference, pp. 285-287 (2002).
John Ritchie Production Group, *Production of Stents* (presentation), 15 pages (Apr. 24, 2003).
Kataoka et al., *Block Copolymer Micelles as Vehicles for Drug Delivery*, Journal of Controlled Release vol. 24, pp. 119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, vol. 37, 391-407 (1999).
Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).
Kelley et al., *Totally Resorbable High-Strength Composite Material*, Advances in Biomedical Polymers, vol. 35, pp. 75-85 (1987).
Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages, no date.
Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).
Kubies et al., *Microdomain Structure In polylactide-block-poly(ethylene oxide) copolymer films*, Biomaterials, vol. 21, pp. 529-536 (2000).
Kutryk et al., *Coronary Stenting: Current Perspectives, a companion to the Handbook of Coronary Stents*, 16 pages (1999).
Lambert et al., *Localized Arterial Wall Drug Delivery From a Polymer-Coated Removable Metallic Stent*, Circulation, vol. 90, No. 2, pp. 1003-1011 (Aug. 1994).
Lemos et al., *Coronary Restenosis After Sirolimus-Eluting Stent Implantation*, Circulation, vol. 108, No. 3, pp. 257-260 (Jul. 22, 2003).
Levy et al., *Strategies For Treating Arterial Restenosis Using Polymeric Controlled Release Implants*, Biotechnology and Bioactive Polymers, pp. 259-268 (1994).
Liu et al., *Drug Release Characteristics of Unimolecular Polymeric Micelles*, Journal of Controlled Release, vol. 68, pp. 167-174 (2000).
Loeb et al., *Parylene as a Chronically Stable, Reproducible Microelectrode Insulator*, IEEE Transactions on Biomedical Engineering, pp. 121-128 (Mar. 1977).
Loh et al., *Plasma Enhanced Parylene Deposition*, Antec, pp. 1099-1103 (1991).
Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).
Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.
Marconi et al., *Covalent bonding of heparin to a vinyl copolymer for biomedical applications*, Biomaterials, vol. 18, No. 12, pp. 885-890 (1997).
Martin et al., *Enhancing the biological activity of immobilized osteopontin using a type-1 collagen affinity coating*, J. Biomed. Mater. Res., vol. 70A, pp. 10-19 (May 14, 2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Moody, *Vacuum Coating Ultrasonic Transducers*, 1 page, Sensors (Dec. 1993).
Muller et al., *Advances in Coronary Angioplasty: Endovascular Stents*, Coronary Artery Disease, vol. 1, No. 4., pp. 438-448 (Jul./Aug. 1990).
Neimark et al., *Hierarchical Pore Structure and Wetting Properties of Single-Wall Carbon Nanotube Fibers*, Nano Letters, vol. 3, No. 3, pp. 419-423 (2003).
Nichols et al., *Electrical Insulation of Implantable Devices by Composite Polymer Coatings*, ISA Transactions, vol. 26, No. 4, pp. 15-18 (1987).
Nordrehaug et al., *A Novel Biocompatible Coating Applied to Coronary Stents*, EPO Heart Journal 14, p. 321 (P1694), Abstr. Suppl. (1993).
Nova Tran™ Custom Coating Services, *Parylene Conformal Coating*, 8 pages, no date.
Olson, *Parylene, a Biostabel Coating for Medical Applications*, Specialty Coating Systems, Inc. Nova Tran™ Parylene Coating Services, no date.
Ozaki et al., *New Stent Technologies*, Progress in Cardiovascular Diseases, vol. XXXIX, No. 2, pp. 129-140 (Sep./Oct. 1996).
Para Tech Coating Company, *Galxyl, Parylene Coatings by Para Tech*, 1 page, no date.
Para Tech Coating Company, *Lab Top® Parylene Deposition System*, 2 pages, no date.

Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./Apr. 2000).

Peng et al., *Role of polymers in improving the results of stenting in coronary arteries*, Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits*, Heart vol. 86, pp. 563-569 (2001).

Pietrzak et al., *Bioabsorbable Fixation Devices: Status for the Craniomaxillofacial Surgeon*, Journal of Craniofacial Surgery, vol. 8, No. 2, pp. 92-96 (1997).

Pietrzak et al., *Bioresorbable Implants—Practical Considerations*, Bone, vol. 19, No. 1, Supplement, pp. 109S-119S (Jul. 1996).

Poncin-Epaillard et al., *Reactivity of a Polypropylene Surface Modified in a Nitrogen Plasma*, Plasma Surface Modification of Polymers pp. 167-180 (1994).

Prabhu, *Computational Modeling in Stent-based Drug Delivery*, Business Briefing: Medical Device Manufacturing & Technology, 4 pages (2004).

Redman, *Clinical Experience with Vasovasostomy Utilizing Absorbable Intravasal Stent*, Urology, vol. XX, No. 11, pp. 59-61 (Jul. 1982).

Refracton Techonolgies, Corp., *Fine Bubble Diffusers*, 2 pages, do date.

Refracton Techonolgies, Corp., *Refractron Advanced Porous Ceramic Product Capabilities*, http://www.refractron.com/ecom/sp/cat=Product+Information, printed Apr. 6, 2004, 3 pages.

Refractron Technologies Corp., http://www.refractron.com/ecom/sp/cat=Custom+Applications, printed Jun. 24, 2003, 1 page.

Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).

Sadhir et al., *The Adhesion of Glow-Discharge Polymers, Silastic And Parylene to Implantable Platinum Electrodes: Results of Tensil Pull tests After Exposure to Isotonic Sodium Chloride*, Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid*, Chemistry Letters, pp. 21-24, (1991).

Schatz, *A View of Vascular Stents*, Circulation, vol. 79, No. 2, pp. 445-457 (Feb. 1989).

Schmidt et al., *Long-term Implants of Parylene-C Coated Microelectrodes*, Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).

Sono Tek Corporation, *AccuMist™ for Single Stent Coating Applications*, http://www.sono-tek.com/biomedical/accumist_stent.html, printed Aug. 2, 2005, 3 pages.

Sono Tek Corporation, *MediCoat™ DES 1000, Benchtop Stent Coating System*, http://www.sono-tek.com/biomedical/medicoat_standalone.html, printed Aug. 2, 2005, 4 pages.

Sono Tek Corporation, *MicroMist for Stent Coating*, http://www.sono-tek.com/biomedical/micromist_stent.html, printed Aug. 2, 2005, 3 pages.

Spagnuolo et al., *Gas 1 is induced by VE-cadherin and vascular endothelial growth factor and inhibits endothelial cell apoptosis*, Blood, vol. 103, No. 6, pp. 3005-3012 (2004).

Specialty Coating Systems, Inc., *The Parylene Press*, 4 pages (Summer 1993).

Specialty Coating Systems, Inc., *The Parylene Press*, 6 pages (Spring 1993).

Specialty Coating Systems, Inc., *The Parylene Press*, 7 pages (Winter 1992).

Specialty Coating Systems, *Parylene and Nova Tran™ Parylene Coating Services, for Unmatched Conformal Coating Performance*, 21 pages, no date.

Specialty Coating Systems, *Parylene, a Biostable Coating for Medical Applications*, 6 pages, no date.

Specialty Coating Systems, *Repair and Recoating of Parylene Coated Printed Circuit Boards*, 15 pages, no date.

Straube, *Moisture, Materials, & Buildings*, HPAC Engineering, pp. 2-7, no date.

Taher, *Capillary interaction between a small thin solid plate and a liquid*, Mechanical and Industrial Engineering, University of Illinois at Urbana-Champaign, 4 pages, no date.

Tamai et al., *Initial and 6-Month Results of Biodegradable Poly-l-Lactic Acid Coronary Stents in Humans*, Circulation, vol. 102, pp. 399-404 (2000).

Trident, Inc., http://www.tridentintl.com/subbody.html, printed Dec. 18, 2000, 1 page.

Trident, Inc., *Product Lines*, http://www.tridentintl.com/products-apps/ultrajet.html, printed Dec. 18, 2000, 3 pages.

Tsuji et al., *Biodegradable Polymeric Stents*, Current Interventional Cardiology Reports vol. 3, pp. 10-17 (2001).

Union Carbide Adhesion Promoters, *Union Carbide A-174 Silane*, 5 pages (Jan. 1968).

Union Carbide Electronics Division, *Parylene Environmentally Compatible Conformal Coatings for Electronic Components Assemblies and Precision Parts*, 14 pages, no date.

Union Carbide, *Abrasion Resistance of Parylene and Other Conformal Circuit Board Coatings*, Parylene Products, No. 4, 13 pages (Oct. 1977).

Union Carbide, *Adhesion Promotion Systems for Parylene*, Parylene Products, No. 15, Revision 1, 8 pages (Oct. 1977).

Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).

Union Carbide, *Fluorescent Parylene Coatings*, Parylene Products, No. 7 Revision 1, 8 pages (Oct. 1977).

Union Carbide, *Fluorescent Parylene Coatings*, Technology Letter, No. 7, 8 pages (Oct. 1973).

Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).

Union Carbide, *Microencapsulation by Vapor Deposition*, Parylene Products, No. 6, 12 pages (Oct. 1977).

Union Carbide, *MIL I 46058, Qualification of Parylene N, C, and D*, Parylene Products, No. 1 Revision 2, 8 pages (Oct. 1977).

Union Carbide, *Parylene Bibliography*, Parylene Products, No. 5, Revision 4, 17 pages (Jan. 18, 1982).

Union Carbide, *Parylene Conformal Coatings for Hybrid Microelectronics*, Parylene Products, No. 9, 23 pages (Oct. 1973).

Union Carbide, *Parylene Pellicles for Space Applications*, Parylene Products, No. 10, 50 pages (Oct. 1977).

Union Carbide, *Parylene Pyrolysis Kinetics*, Parylene Products, No. 11, 12 pages (Oct. 1977).

Union Carbide, *Parylene Pyrolysis Kinetics*, Technology Letter, No. 11, 12 pages (May 1974).

Union Carbide, *Parylene Removal with Oxygen Plasmas*, Parylene Products, No. 18, 7 pages (Aug. 1977).

Union Carbide, *Printed Circuit Board Masking Techniques for Use with Parylene*, No. 14, Revision 1, 11 pages (Oct. 1977).

Union Carbide, *Solvent Resistance of the Parylenes*, Parylene Products, No. 12, Revision 1, 5 pages (Oct. 1977).

Union Carbide, *The Selective Removal of Parylene by Plasma Etching*, No. 13, Revision 1, 7 pages (Oct. 1977).

Union Carbide, *Thermal Endurance of the Parylenes in Air*, Parylene Products, No. 16, 4 pages (Mar. 1976).

Union Carbide, *Vapor Phase Adhesion Promotion Systems*, Parylene Products, No. 17, Revision 1, 11 pages (Oct. 1977).

van Beusekom et al., *Coronary Stent Coatings*, Coronary Artery Disease, vol. 5, No. 7, pp. 590-596 (Jul. 1994).

Vapor Inc., *Vapore-Jet™ Capillary Pump—How it Works*, http://www.vapore.com/tech_howto.htm, printed Aug. 13, 2003, 2 pages.

Völkel et al., *Targeting of immunoliposomes to endothelial cells using a single—chain Fv fragment directed against human endoglin (CD105)*, Biochemica et Biophysica Acta, vol. 1663, pp. 158-166 (Apr. 15, 2004).

von Recum et al., *Degradation of polydispersed poly(L-lactic acid) to modulate lactic acid release*, Biomaterials, vol. 16, pp. 441-445 (1995).

Wilensky et al., *Methods and Devices for Local Drug Delivery in Coronary and Peripheral Arteries*, Trends Cardiovasc. Med., vol. 3, No. 5, pp. 163-170 (1993).

Wong et al., *An Update on Coronary Stents*, Cardio, 8 pages (Feb. 1992).

World Precision Instruments, Inc., http://www.wpiinc.com/WPI_Web/Pumps/pneumatic_Fig.gif, printed Sep. 30, 2002, 1 page.

World Precision Instruments, Inc., *Nanoliter Injector*, http://www.wpiinc.com/WPI_Web/Microinjection/Nanoliter_Injector.html, printed Jun. 10, 2005, 3 pages.

World Precision Instruments, Inc., *Nanoliter Injector*, http://www.wpi-europe.com/products/microinjection/nanoliter.htm printed Jun. 10, 2005, 2 pages.

World Precision Instruments, Inc., *Pneumatic PicoPumps*, http://www.wpieurope.com/products/microinjection/picopumps.htm, printed Jun. 10, 2005, 4 pages.

World Precision Instruments, Inc., *Pneumatic PicoPumps*, http://www.wpiinc.com/WPI_Web/Microinjection/Pneumatic_PicoPumps.html, printed Jun. 10, 2005, 4 pages.

Yau et al., *Modem Size-Exclusion Liquid Chromatography*, Wiley-Interscience Publication, 9 pages (1979).

Yokoyama et al., *Characterization of physical entrapment and chemical conjugation of adriamycin in polymeric micelles and their design for in vivo delivery to asolid tumor*, Journal of Controlled Release, vol. 50, pp. 79-92 (1998).

Yuen et al., *Tissue response to potential neuroprosthetic materials implanted subdurally*, Biomaterials, vol. 8, pp. 57-62 (Mar. 1987).

Zhmud et al., *Dynamics of Capillary Rise*, Journal of Colloid and Interface Science, vol. 228, pp. 263-269 (2000).

Zimarino et al., *Analysis of Stent Edge Restenosis with Different Forms of Brachytherapy*, The American Journal of Cardiology, vol. 89, pp. 322-325 (Feb. 1, 2002).

Zylberman et al., *Comparative Study of Electroless Co(W,P) and Co(Mo,P) Thin-Films for Capping and Barrier Layers for Cu Metallization*, 2002 Advanced Metallization Conference, 2 pages, no date.

\* cited by examiner

SELECTIVE COATING OF MEDICAL DEVICES

CROSS REFERENCE

This is a divisional application of U.S. application Ser. No. 09/697,106, now U.S. Pat. No. 6,783,793, which was filed on Oct. 26, 2000.

FIELD OF THE INVENTION

The present invention relates to the coating of an implantable device. More specifically, this invention relates to a method for selective coating of an intraluminal implantable device, such as a stent or graft.

BACKGROUND

Occlusion of blood vessels reduces or blocks blood flow. During the course of atherosclerosis, for example, growths called plaques develop on the inner walls of the arteries and narrow the bore of the vessels. An emboli, or a moving clot, is more likely to become trapped in a vessel that has been narrowed by plaques. Further, plaques are common sites of thrombus formation. Together, these events increase the risk of heart attacks and strokes.

Traditionally, critically stenosed atherosclerotic vessels have been treated with bypass surgery in which veins removed from the legs, or small arteries removed from the thoracic cavity, are implanted in the affected area to provide alternate routes of blood circulation. More recently, implantable devices, such as synthetic vascular grafts and stents, have been used to treat diseased blood vessels.

Synthetic vascular grafts are macro-porous vessel-like configurations typically made of expanded polytetrafluoroethylene (ePTFE), polyethylene terephthalate (PET), polyurethane (PU), or an absorbable polymer. Grafts made of ePTFE or PET are very non-wetting materials when introduced into an aqueous environment, causing difficulty in impregnating the materials. In addition, grafts made of ePTFE or PET typically are permanently implanted in the body, while grafts made of an absorbable polymer bioabsorb over time. A graft may be positioned into the host blood vessel as a replacement for a diseased or occluded segment that has been removed. Alternatively, a graft may be sutured to the host vessel at each end so as to form a bypass conduit around a diseased or occluded segment of the host vessel.

Percutaneous transluminal coronary angioplasty (PTCA) is a procedure for treating heart disease in which a catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the vessel. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neointimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

Intravascular stents are sometimes implanted within vessels in an effort to maintain the patency thereof by preventing collapse and/or by impeding restenosis. Implantation of a stent is typically accomplished by mounting the stent on the expandable portion of a balloon catheter, maneuvering the catheter through the vasculature so as to position the stent at the desired location within the body lumen, and inflating the balloon to expand the stent so as to engage the lumen wall. The stent maintains its expanded configuration, allowing the balloon to be deflated and the catheter removed to complete the implantation procedure. A covered stent, in which a graft-like covering is slip-fit onto the stent, may be employed to isolate the brittle plaque from direct contact with the stent, which is rigid.

To reduce the chance of the development of restenosis, therapeutic substances may be administered to the treatment site. For example, anticoagulant and antiplatelet agents are commonly used to inhibit the development of restenosis. In order to provide an efficacious concentration to the target site, systemic administration of such medication may be used, which often produces adverse or toxic side effects for the patient. Local delivery is a desirable method of treatment, in that smaller total levels of medication are administered in comparison to systemic dosages, but are concentrated at a specific site. Therefore, local delivery may produce fewer side effects and achieve more effective results.

One commonly applied technique for the local delivery of a therapeutic substance is through the use of a medicated implantable device, such as a stent or graft. Because of the mechanical strength needed to properly support vessel walls, stents are typically constructed of metallic materials. The metallic stent may be coated with a polymeric carrier, which is impregnated with a therapeutic agent. The polymeric carrier allows for a sustained delivery of the therapeutic agent.

Various approaches have previously been used to join polymers to metallic stents, including dipping and spraying processes. In one technique, the stent is first formed in a flat sheet, placed in a solution of polyurethane, and heated for a short period of time. Additional polyurethane solution is applied on top of the flat sheet, and the stent is again heated. This process produces a polyurethane film over the surface of the stent, and excess film is manually trimmed away. In one variation of this technique, microcapsules containing therapeutic agents are incorporated into the polyurethane film by adding the microcapsules to the polyurethane solution before heating.

In another technique, a solution is prepared that includes a solvent, a polymer dissolved in the solvent, and a therapeutic agent dispersed in the solvent. The solution is applied to the stent by spraying the solution onto the stent using an airbrush. After each layer is applied, the solvent is allowed to evaporate, thereby leaving on the stent surface a coating of the polymer and the therapeutic substance. Use of this spraying technique to apply a thick coating may result in coating uniformity problems, so multiple application steps are sometimes used in an attempt to provide better coating uniformity.

In yet another coating technique, a solution of dexamethasone in acetone is prepared, and an airbrush is used to spray short bursts of the solution onto a rotating wire stent. The acetone quickly evaporates, leaving a coating of dexamethasone on the surface of the stent.

The above-described methods often have difficulty in applying an even coating on the stent surfaces. One common result when using these spraying or immersion processes is that the aqueous coating tends to collect in crevices, apertures, or cavities in the framework of the stent, resulting in an uneven coating having an uncontrollably variable coating thickness. In particular, an excess amount of coating is often entrained in the angle between two intersecting struts of a stent, which is sometimes called "webbing" or "pooling." The deposition of excessive amounts of therapeutic agents results in a poor surface area to volume ratio relative to conformal coatings. When such a coating experiences uncontrolled drying, drying artifacts may result in drug crystal formation.

The use of multiple applications of a fine, diffuse spray may produce a more controllable, even coating than immersion techniques. However, the diffuse application results in much of the coating substance not coating the stent and instead being released into the air. This inefficient use of the coating substance wastes the coating substance, which may be quite expensive, and increases the exposure of the air brush operator to the coating substance.

In addition, existing methods for coating implantable devices do not provide effective techniques for applying coatings of different substances onto different portions of the surface of the implantable device.

SUMMARY

In view of the above, there is a need to provide an improved method for coating medical devices which produces superior coating uniformity and control of the location of the coating without an excessive loss of materials. It is also desirable that the coating method can be used on a variety of implantable devices with aqueous or solvent-based coating substances. In particular, it is desired that therapeutic or bioactive substances, such as compositions of a polymer, solvent, and therapeutic substance, can be used to coat stents.

In accordance with various aspects of the present invention, the invention relates to a method for coating an implantable device. In one embodiment, the method comprises applying a first coating substance on a first portion of a surface of the implantable device, applying a second coating substance on a second portion of a surface of the implantable device, and rotating the implantable device about an axis of rotation. In another embodiment, a first coating substance is applied to an interior surface of a cylindrical implantable device, such as a stent or graft, and a second coating substance is applied to an exterior surface. A centrifuge step is performed so that the first coating substance is preferentially and uniformly applied on the interior surface of the implantable device and the second coating substance is preferentially and uniformly applied on the exterior surface of the implantable device.

Various embodiments of the described method enable highly viscous materials to be coated onto implantable devices. Viscous materials are not usually amenable to conventional coating methods such as dipping or spraying, because of the viscous material's propensity to accumulate in an uneven layer. However, the addition of a centrifugation step after dipping the implantable device in the viscous coating material can transform the uneven masses into a smooth, even coating.

Embodiments of the method also enable uniform coatings to be applied to implantable devices with improved repeatability, thereby improving coating uniformity between batches of implantable devices. With conventional manually-applied spray-coating techniques, operator error or inconsistency may result in different coating thicknesses between batches of stents. The centrifugation processes can reduce unwanted gross deposition of coating substances and enable high reproducibility of the coating quality.

Embodiments of the method also enable multiple stents to be processed simultaneously. Unlike manually-applied airbrush coating methods, in which stents are coated individually or in small groups, large batches of stents can be simultaneously immersed in the coating solution, simultaneously rotated in the centrifuge device, and simultaneously heated in an oven, thereby increasing throughput.

Embodiments of the method also may improve operator safety when coating implantable devices with hazardous materials. It is generally not desirable to spray coat an implantable device with toxic or radioactive coating substances, because of the increased exposure of the operator to the airborne hazardous coating substance. Dipping and centrifuging the implantable device as described above can decrease the amount of handling required for the coating process, resulting in reduced environmental contamination.

Embodiments of the method may also mitigate defects due to handling of the implantable device. In conventional spray processes, the implantable device is held aloft using one or two clamps or fixtures while the coating substance is sprayed onto the device. The point where these clamps contact the device may be masked from receiving the spray, resulting in defects in the coating. In contrast, the centrifuge container has minimal contact with the implantable device during the centrifuge process.

In another embodiment of the present invention, the invention relates to a drug loaded implantable device comprising two or more coating substances, each of the substances applied to portions of the device. In one embodiment, the portions are exterior surfaces of the device. In yet another embodiment, one of the portions is an exterior surface and another of the portions is an interior surface of the device. Further, one of the substances applied to the device can be a first substance that evenly coats a first portion of the device. Another of the substances can be a second substance that evenly coats a second portion of the device.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION

Figure 1:
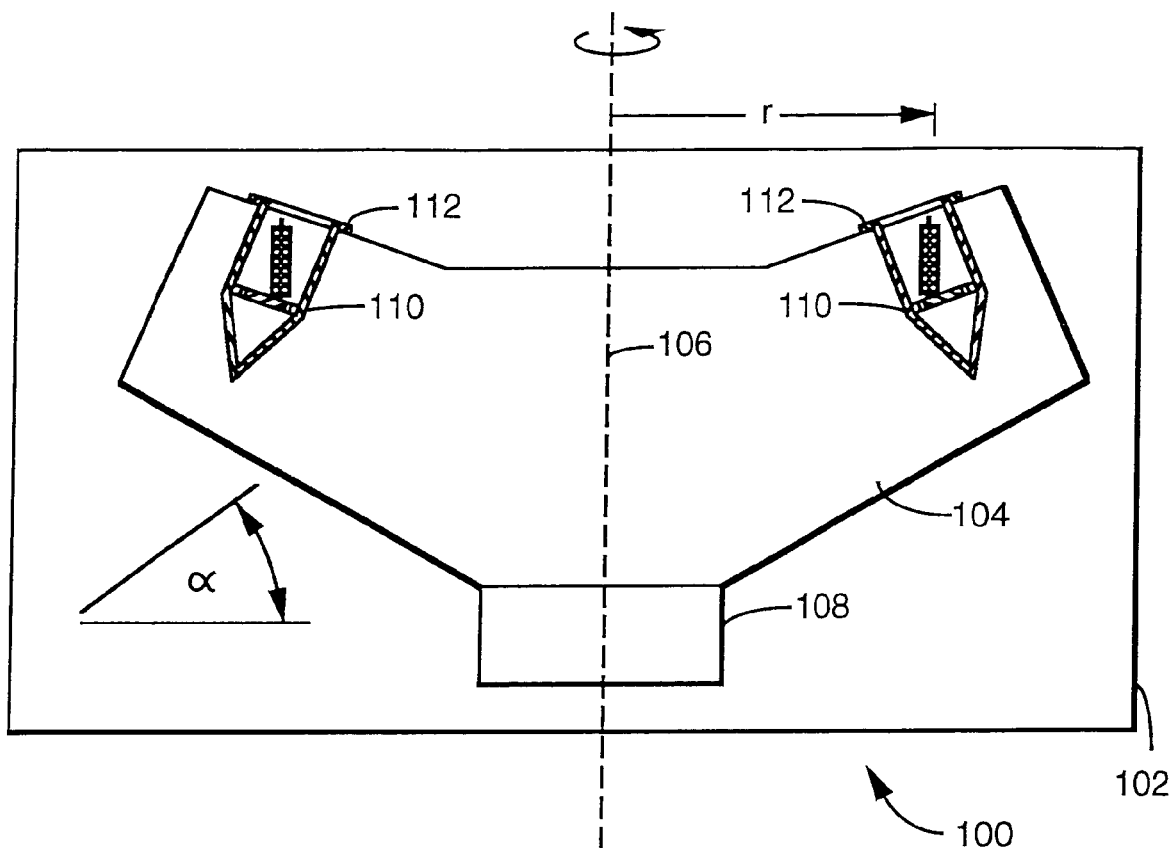
FIG. 1 illustrates in plan view a cross-section of an embodiment of a centrifuge system.

The following description is meant to be illustrative only and not limiting. Other embodiments of this invention will be apparent to those of ordinary skill in the art in view of this description.

The figures generally illustrate the techniques used to apply coatings to a stent in accordance with an embodiment of the present invention. Although the illustrated and described embodiments may relate to wire-based stents, any of a variety of implantable devices may be subjected to the coating process described herein, including, but not limited to, wire-based stents, tubular stents, rolled-sheet type stents, stent coverings, vascular grafts, or any implantable device having a complicated architecture which is not amenable to standard coating.

The materials from which such stents are formed may include metals such as, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent also may be made from virtually any biocompatible material, such as bioabsorbable or biostable polymers.

Vascular grafts may be used to replace, bypass, or reinforce diseased or damaged sections of a vein or artery. These grafts can be made from any suitable material including, but not limited to, highly open-pored materials such as polymers of expanded polytetrafluoroethylene (ePTFE) and polyethylene terephthalate (PET), or less porous materials such as polyurethanes, absorbable polymers, and combinations or variations thereof. Grafts may be formed using a lyophilization process. Polyurethanes from which the graft may be made include, but are not limited to, Biomer, BioSpan® polyurethane (manufactured by Polymer Technology Group, Berkeley, Calif.; referenced herein after as "BioSpan®"), and Elastion. Absorbable polymers from which the graft may be made include, but are not limited to, polycaprolactone (PCL), poly(lactic acid) (PLA), poly(glycolic acid) (PGA), polyanhydrides, polyorthoesters, polyphosphazenes, and components of extracellular matrix (ECM). In such an embodiment, additional interstices can be formed in the graft by any conventional methods known to one of ordinary skill in the art, including exposure of the graft to a laser discharge to form a pattern of pores.

In other embodiments, the implantable device to be coated is a covering for a self-expandable or balloon-expandable stent. This covering can be formed of materials similar to those from which the above-described graft may be formed.

Various types of coating substances may be applied to an implantable device in accordance with the present invention. In one embodiment, the coating substance includes a polymer loaded with a therapeutic substance. The terms "polymer," "poly," and "polymeric" as used herein mean the product of a polymerization reaction and are inclusive of homopolymers, copolymers, terpolymers, etc., whether natural or synthetic, including random, alternating, block, graft, crosslinked, blends, compositions of blends and variations thereof. The term "pre-polymer" refers to a low molecular weight material, such as oligomers, that can be further polymerized regardless of the mechanism of polymerization.

The polymer or combination of polymers can be applied to a stent based on the polymer's or polymers' ability to carry and release, at a controlled rate, various therapeutic agents such as antithrombogenic or anti-proliferative drugs. The polymeric material is most suitably biocompatible, including polymers that are non-toxic, non-inflammatory, chemically inert, and substantially non-immunogenic in the applied amounts. The polymer is typically either bioabsorbable or biostable. A bioabsorbable polymer breaks down in the body and is not present sufficiently long after implantation to cause an adverse local response. Bioabsorbable polymers are gradually absorbed or eliminated by the body by hydrolysis, metabolic process, bulk erosion, or surface erosion. Examples of bioabsorbable materials include but are not limited to polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(etheresters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene® and Parylast® (available from Advanced Surface Technology of Billerica, Mass.), polyurethane, such as a segmented polyurethane solution containing a dimethylacetamide (DMAc) solvent developed by the Polymer Technology Group, Inc. of Berkeley, Calif., and known by the trade name BioSpan®, polyethylene, polyethlyene teraphthalate, ethylene vinyl acetate, silicone and polyethylene oxide (PEO).

The expression "therapeutic agent" as used herein broadly refers to an agent or substance including, but not limited to, a therapeutic substance, a polymer impregnated with therapeutic substance, radioactive isotope, and radiopaque material, that possesses desirable therapeutic characteristics. The therapeutic agent may be, for example, antineoplastic, antimitotic, antiinflammatory, antiplatelet, anticoagulant, antifibrin, antithrombin, antiproliferative, antibiotic, antioxidant, and antiallergic substances, as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany) methotrexate, azathioprine, actinomycin-D, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, Trapidil antiplatelet (manufactured by DAITO Corporation, Japan; referenced herein after as "Trapidil"), genetically engineered epithelial cells, and dexamethasone. In yet other embodiments, the therapeutic substance is a radioactive isotope used in radiotherapeutic procedures. Examples of radioactive isotopes include, but are not limited to, phosphoric acid ($H_3P^{32}O_4$), palladium ($Pd^{103}$), cesium ($Cs^{131}$), and iodine $I^{125}$).

While the preventative and treatment properties of the foregoing therapeutic substances or agents are well known to those of ordinary skill in the art, the substances or agents are provided by way of example and are not meant to be limiting. Other therapeutic substances are equally applicable for use with the disclosed embodiments. For example, while many of the herein-described therapeutic agents have been used to prevent or treat restenosis, they are provided by way of example and are not meant to be limiting, since other drugs or coatings may be developed which are equally applicable for use with embodiment of the present invention.

In other embodiments, the coating is an aqueous solution of a therapeutic substance that does not contain a polymer matrix, for example, an aqueous solution of heparin. This aqueous solution can be applied to the stent and allowed to dry, thereby forming a heparin coating on the stent.

In addition to a polymer and a therapeutic agent, the coating substance may also include a solvent. The solvent can be virtually any solvent that is compatible with the implantable device to be coated. Examples of suitable solvents include but are not limited to dimethyl sulfoxide, dimethyl formamide, tetrahydrofuran, dimethyl acetamide, trichloroethane, acetone, ethanol, methanol, isopropanol, and ethyl acetate.

FIG. 1 shows a cross-section of an exemplary centrifuge system 100 in accordance with an embodiment of the present invention. Centrifuge system 100 includes a centrifuge device 102, which includes a rotatable rotor 104 for rotation about an axis 106, and a motor 108 which drives rotor 104 to rotate about axis 106. Centrifuge models 5410, 5415, 5417, 5804, and 5810, sold by Eppendorf Scientific, Inc., of Westbury, N.Y., may be used, for example, as centrifuge device 102. Exemplary centrifuge devices 102 provide rotational speeds of up to, for example, 14,000 rotations per minute ("RPM"). Rotor 104 includes a plurality of hollow chambers 110 circularly arranged about axis 106. Each chamber 110 is sized to receive a centrifuge container 112. Various centrifuge devices 102 available on the market are capable of centrifuging large numbers of centrifuge containers 112 simultaneously.

Figure 2:
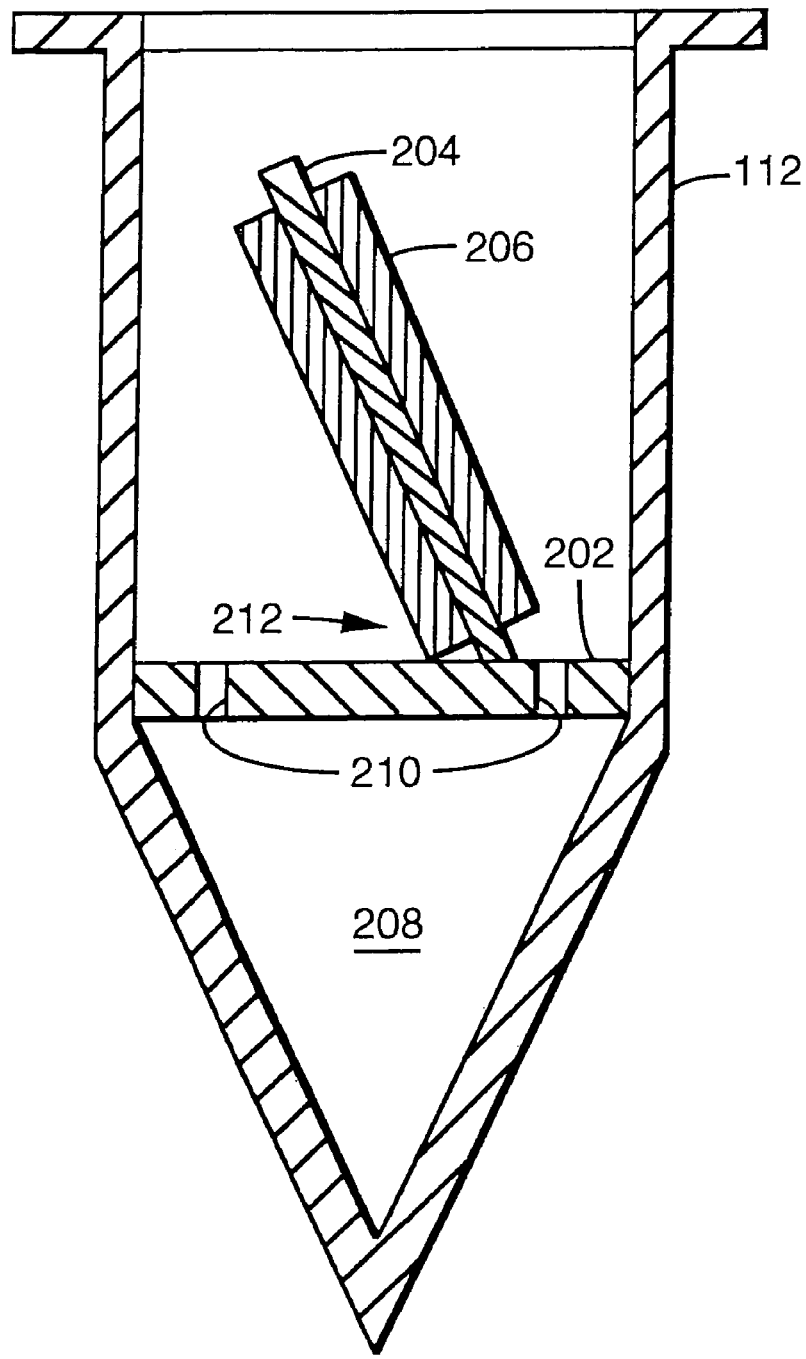
FIG. 2 is a cross-section in plan view of an embodiment of a centrifuge container.

FIG. 2 shows in greater detail a cross-section of an exemplary centrifuge container 112. Centrifuge container 112 can be formed using a conventional centrifuge tube that has been modified as described below. A support 202 is provided towards the bottom of centrifuge container 112, and a mandrel 204 is preferably mounted thereon. In this embodiment, mandrel 204 is a rod. Mandrel 204 is inserted into the interior of the implantable device to be coated, such as a cylindrical stent 206. Mandrel 204 holds stent 206 and prevents stent 206 from contacting the interior walls of centrifuge container 112. Support 202 separates stent 206 from runoff reservoir 208, which is provided at the bottom of centrifuge container 112. Drainage openings 210 may be provided in support 202.

As can be seen in the embodiment shown in FIGS. 1-2, mandrel 204 is tilted such that when each centrifuge container 112 is mounted in centrifuge system 100, stents 206 are positioned such that their longitudinal axes are nearly parallel to axis of rotation 106. This may provide a more even coating on stents 206 after centrifugation. In alternative embodiments, mandrels 204 may have a different tilt angle relative to the central axes of centrifuge containers 112, or may have no tilt at all.

Figure 3:
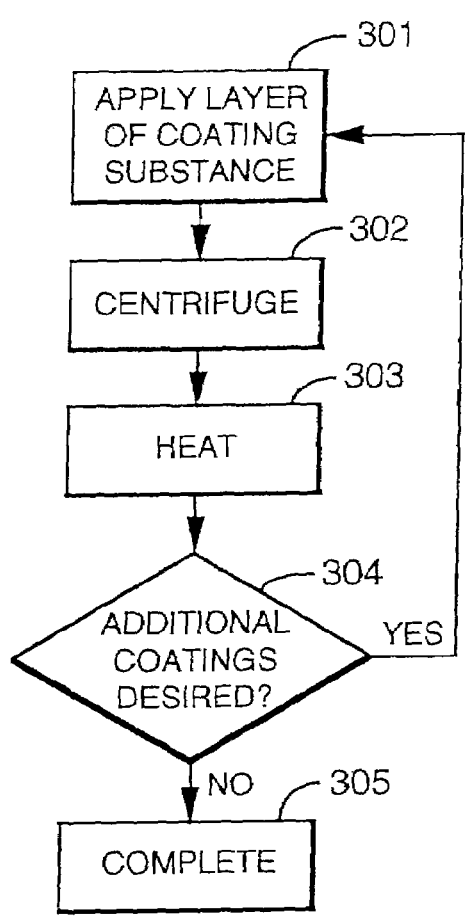
FIG. 3 is a flowchart of an embodiment of a coating process.
Figure 4:
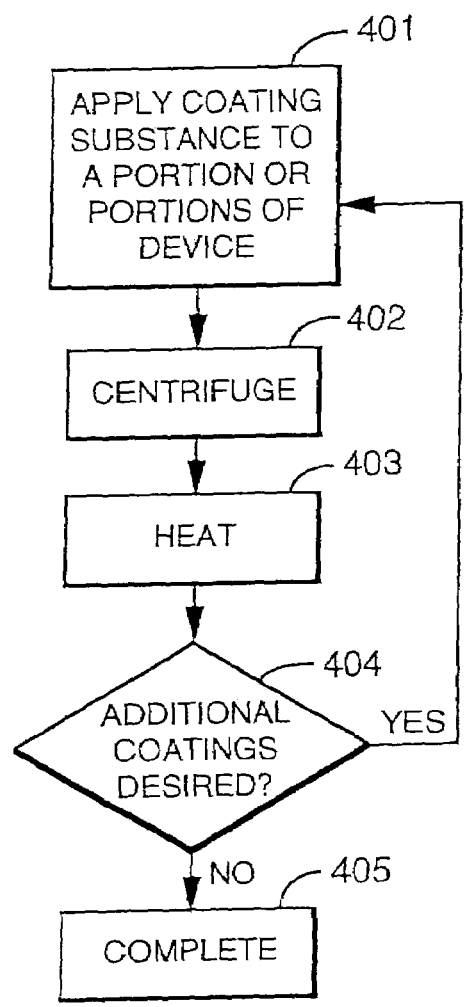
FIG. 4 is a flowchart of an alternative embodiment of a coating process.

FIGS. 3 and 4 are flowcharts illustrating exemplary methods of coating an implantable device in accordance with an embodiment of the present invention. For the sake of example, the implantable device described with respect to FIGS. 1-4 is a stent, but the method also may be applied to various other implantable devices discussed above.

Figure 5:
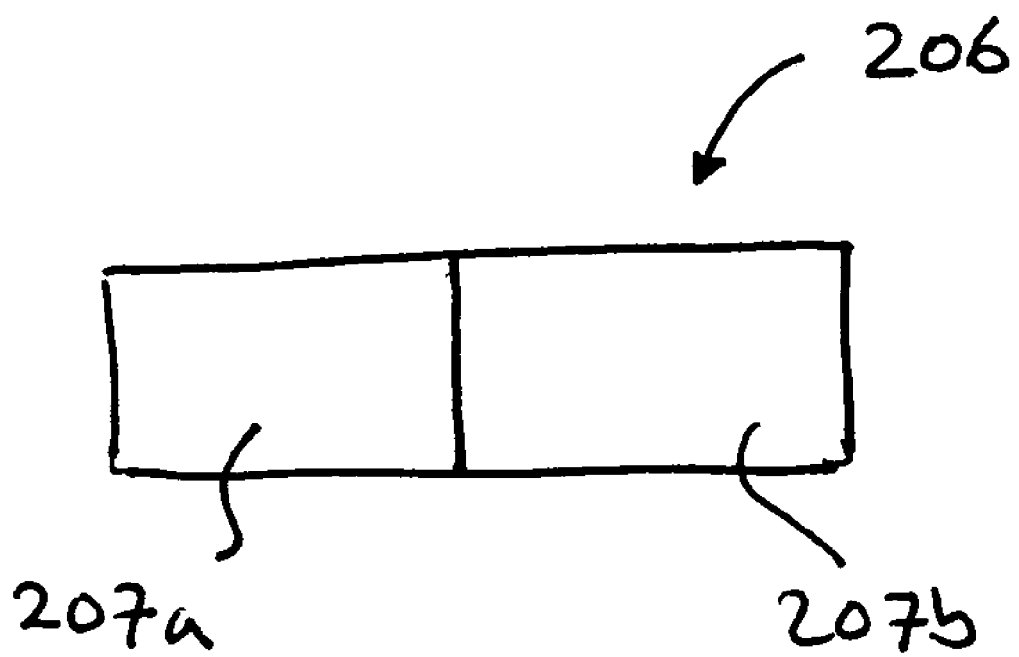
FIG. 5 is one embodiment of a stent having a first and second coating.

FIG. 5 illustrates a stent 206 having a first coating 207a and a second coating 207b. The first coating 207a comprises a first substance disposed along a first segment of the body of the stent 206 and the second coating 207b comprises a second substance disposed along a second segment of the body of the stent 206.

Referring to FIG. 3, in act 301, a first coating is applied to stent 206. The coating may be applied by injecting, spraying or immersing stent 206 with a liquid coating substance using techniques similar to those described in the background section above. The term "liquid" as used herein refers to substances having sufficient fluidity such that the substance can flow over the surface of stent 206 when processed through the further acts described below. "Liquid" is not intended to limit the coating substance to water-based substances or to low viscosity materials. Even highly viscous substances such as a hyaluronic acid solution (e.g., 1% hyaluronic acid), high molecular weight polyethylene glycol solution, gelatin solution, or poly(lactic) acid in 1,1,2 trichloroethane (e.g., 10% poly(lactic) acid) are included within the term.

As occurs with conventional coating techniques, the spraying or immersion of stent 206 in the coating substance typically results in a non-uniform coating, with webbing being observable between struts on stent 206. The term "strut(s)" as used herein includes the elongated elements and interconnecting elements of stent 206. In act 302, the still-wet stent 206 is inserted onto mandrel 204 in centrifuge container 112 such that mandrel 204 extends through the hollow interior of stent 206. Centrifuge container 112 is then inserted into chamber 110 of centrifuge system 100 (FIG. 1), and centrifuge system 100 is used to rotate stent 206 about axis 106 at high speeds. Centrifuge system 100 includes a plurality of rotatable chambers 110, such that multiple coated stents 206 can be centrifuged simultaneously, thereby increasing processing throughput.

The rotation of chambers 110 at high speeds creates a centrifugal force upon the coating substance that previously was applied to the surface of stent 206. Centrifugal force causes excess accumulations of coating substance, particularly the portions entrained between the struts of stent 206, to evenly redistribute over stent 206. Redistribution of the coating substance over the surface of stent 206 provides a more uniform coating free of webbing.

The centrifugation of stent 206 may result in some excess coating substance being removed from the surface of stent 206. Drainage openings 210 are provided in support 202 so that the runoff coating substance can flow from the upper portion of centrifuge container 112 into runoff reservoir 208. The channeling of runoff coating substance into runoff reservoir 208 prevents the coating substance from accumulating at the bottom end 212 of stent 206, which could lead to a non-uniform coating. Runoff coating substance can be recovered from runoff reservoir 208 and reused to coat additional stents 206. The recycling of the coating substance can produce significant cost savings when an expensive therapeutic agent is being used.

In alternative embodiments, different structures are provided to effectuate the flow of runoff coating substance into runoff reservoir 208. In one embodiment, support 202 is square-shaped, such that when support 202 is fitted into a centrifuge container 112 which is cylindrical in shape, runoff coating substance can flow around the openings formed between the edges of square support 202 and the circular interior of centrifuge container 112. In another embodiment, support 202 comprises a mesh platform, such that fluid can freely flow through support 202 to pass into reservoir 208. Numerous other variations are possible.

In act 303, coated, centrifuged stent 206 is immediately placed into a conventional oven for heating. Heating evaporates solvents that might be present in the coating substance, thereby forming a solid coating on the surface of stent 206. Heating act 303 can improve the adhesion of the coating substance to the metal forming metallic stents 206, and can also provide a better equilibrium for the solid phase drug distribution in the matrix of the coating substance. Heating act 303 might be used, for example, when coating stent 206 with a composition of ethylene vinyl alcohol copolymer with dimethyl sulfoxide, as will be described in greater detail in the example below. In alternative embodiments, no heating act is used, and stent 206 may be implanted immediately after centrifugation act 302. The use of a heating step and the parameters of such a step will vary with the application.

In act 304, it is determined whether one or more additional layers of coating substance is to be applied to stent 206. If so, the process returns to act 301, and another layer of coating substance is applied. Multiple layers of coating substance may be applied to produce a more uniform coating with fewer defects. Each layer can be formed very thin and uniform, and subsequent layers can be added to increase the overall loading onto stent 206. Moreover, the use of multiple layers can provide enhanced control over the release rate of the coating. Finally, when the desired number of layers have been applied, the process is completed at act 305, and stent 206 may be packaged for delivery or immediately implanted into a patient's body using techniques well-known to those of ordinary skill in the art.

In another embodiment shown in FIG. 4, act 401 involves applying a first coating substance to a portion of stent 206. As previously described, the coating may be applied by injecting, spraying or immersing stent 206 with an aqueous coating substance using techniques similar to those described in the background section above. In act 402, the still-wet stent 206 is inserted onto mandrel 204 in centrifuge container 112 such that mandrel 204 extends through the hollow interior of stent 206. Centrifuge container 112 is then inserted into chamber 110 of centrifuge system 100 (FIG. 1), and centrifuge system 100 is used to rotate stent 206 about axis 106 at high speeds.

The rotation of chambers 110 at high speeds creates a centrifugal force upon the coating substance that previously was applied to the surface of stent 206. Centrifugal force causes excess accumulations of coating substance, particularly the portions entrained between the struts of stent 206, to be more evenly redistributed over stent 206. Redistribution of the coating substance over the surface of stent 206 provides a more uniform coating free of webbing.

The centrifugation of stent 206 may result in some excess coating substance being removed from the surface of stent 206. Drainage openings 210 are provided in support 202 so that the runoff coating substance can flow from the upper portion of centrifuge container 112 into runoff reservoir 208. The channeling of runoff coating substance into runoff reservoir 208 prevents the coating substance from accumulating at the bottom end 212 of stent 206, which could lead to a non-uniform coating. This runoff coating substance can be recovered from runoff reservoir 208 and reused to coat additional stents 206. The recycling of the coating substance can produce significant cost savings when an expensive therapeutic agent is being used.

In act 403, coated, centrifuged stent 206 is immediately placed into a conventional oven for heating. In alternative embodiments, no heating act is used, and stent 206 may be implanted immediately after centrifugation act 302. The use of a heating step and the parameters of such a step will vary with the application.

In act 404, whether additional coating substance is to be applied to a portion or portions of stent 206 is determined. If so, the process returns to act 401, and additional coating substance is applied to a portion or portions of stent 206. Each portion of stent 206 can be covered in a different coating substance. For example, in one embodiment a first end of stent 206 is dipped into a first coating substance. Stent 206 is then centrifuged to provide an even coating at the first end. Next, the second end of stent 206 is dipped into a second coating substance, and stent 206 is again centrifuged to provide an even coating at the second end.

In another embodiment, a first coating substance is applied to an interior portion or surface of stent 206 and a second coating substance is applied to an exterior surface or portion of stent 206. In addition to a general stent structure, the following coating configuration also applies to other devices, including a stent graft or sheath covered stent. Further, the structural configuration of the stent graft or sheath covered stent also prevents the two coating substances from intermixing. For this embodiment, the stent 206 is inserted onto a mandrel in the centrifuge container and a volume or drop (i.e., approximately 20 microliters) of first coating substance is dripped into the interior portion of the stent. As such, the substance generally coats the interior portion as the viscous substance drips through the stent. Second and third drops of the first coating substance are also applied in a similar manner, for a total of approximately 60 microliters of substance coating the interior portion of the stent. The stent is then centrifuged and dried in an oven at approximately 50° C. for 5 hours. Approximately 60 microliters are similarly applied to the exterior of the stent, centrifuged and dried according to the above procedure to produce an evenly interior and exterior coated stent.

When the desired number of layers have been applied, the process is completed at act 405, and stent 206 may be packaged for delivery or immediately implanted into a patient's body using techniques well-known to those of ordinary skill in the art.

The application of one or more coating substances to different portions of the stent or graft precludes potential physical and/or chemical interactions from occurring between multiple substances. In addition, this coating technique also allows variable layers of the same or different substances to be applied to specific portions of the stent, thereby providing enhanced site-specific treatment of various disease states and/or conditions.

For example, stents uniformly coated with radioactive materials that limit cell proliferation have been used to treat restenosis. However, one side effect of this treatment method is the occurrence of a "candy-wrapper" effect at the treatment site. In general, the candy-wrapper effect is characterized by enhanced restenosis at the ends or edges of the radioactive stent that cause the ends of the stent to twist and contract in a radially inward direction. The abrupt change in radioactive levels at the edges of the stent, e.g. between tissue contacting the radioactive stent versus tissue not contacting the stent, is thought to further stimulate the proliferation of smooth muscle cells at these sites.

One method of mitigating this effect is to apply variable layers of radioactive material along the surface of the stent. In general, the level or amount of radiation at a tissue site is proportional to the number of layers of radioactive substance applied to the corresponding portion of the stent. As such, gradually decreasing the number of radioactive material layers towards the ends of the stent provides a smooth transition in radiation amounts between adjacent tissue cells. For example, for material delivering a radiation dosage of 10-100 gray (Gy) approximately 1 to 5 layers of material are applied to the central portion of the stent. Successively decreasing numbers of layers of the radioactive material are applied to the stent, terminating at the end or edge portions of the stent having only 1 to 2 layers of material. Other radioactive materials and layer variations, though not expressly disclosed, may also be used. This, in turn, inhibits cell stimulation and proliferation in tissue contacting the stent surface and portions of surrounding tissues, thereby preventing the occurrence of the candy-wrapper effect.

Alternatively, materials having different levels of radioactive substances may also be used to counteract the candy wrapper effect. For this embodiment, materials containing higher levels or dosages of radioactive substances are applied in a single layer near the central portion of the stent. Likewise, single layers of lower radioactive substances, whereby the radioactive levels are successively decreasing in the direction away from the central portion of the stent, are also applied to the surface of the stent. Exemplary dosage ranges of radioactive substances, whereby the high dosage range represents materials applied to the central portion of the stent and the low dosage range represents materials applied to the edge sections of the stent, are 50 Gy to 100 Gy and 10 Gy to 30 Gy, respectively. As described above, the stent configuration prevents cell stimulation and proliferation in tissue contacting the stent and, also, in surrounding tissues.

In yet another embodiment, the edges of the stent contain increased levels of radioactivity compared to the central portion of the stent. The dosage of radioactivity at the edges of the stent is configured to inhibit stimulation and proliferation of surrounding cells. As such, the radioactive material arrests cell division not only at the edges of the stent, but also in the surrounding tissue. In general, the level of radioactive substance applied to the end portions is approximately 500% to 1,000% greater than the level of radioactive substance applied to the central portion of the stent. As such, the increased dosage of radioactive material applied to the end portions of the stent inhibits the occurrence of the candy wrapper effect.

Grafts and stent coverings may include a large number of interstices, which cause these devices to have a generally permeable characteristic. In accordance with various embodiments of the present invention, permeable grafts and stent coverings can be coated with a coating substance, such as those described above, and then placed into a centrifuge for centrifugation. The centrifugation process provides improved perfusion of the coating substance through the interstices of the graft or stent covering, particularly when the devices are formed of a highly hydrophobic material.

In another embodiment, a process for applying a hydrogel coating to a graft or stent covering is provided. When applying a hydrogel coating, a coating substance containing at least one crosslinkable pre-polymer and a first fluid in which the pre-polymer is soluble is prepared. The pre-polymer should be in true solution, saturated, or super-saturated with the first fluid. Exemplary crosslinkable pre-polymers include, but are not limited to, polyethylene glycol (PEG) diacrylate, hyaluronic, and pluronic. The concentration of pre-polymer in the composition should be selected such that it is high enough to ensure effective crosslinking of the pre-polymer since a solution too dilute may not form a crosslinked hydrogel. An implantable device may then be dipped into this pre-polymer coating substance. Alternatively, prior to application of the pre-polymer, the implantable device may be perfused with a low surface energy solvent such as, for example, acetone or ethanol, which effectuates improved perfusion of the pre-polymer solution through the interstices of the implantable device.

After the implantable device is dipped into the pre-polymer solution, the implantable device is placed in a centrifuge container and loaded into a centrifuge system, similar to the centrifuge container 112 and centrifuge system 100 described above. Centrifuging the coated implantable device spreads the viscous pre-polymer solution evenly across the surface of the implantable device and into the interstices or crevices therein.

The pre-polymer is cured to form a hydrogel coating on the implantable device. Curing may be accomplished photochemically using ultraviolet or visible irradiation and a photoinitiator, thermally, or by moisture curing at room temperature. The practice of these and other suitable curing procedures is well known to those of ordinary skill in the art.

In yet another embodiment, the coating method of the present invention can be used to provide a physician with greater flexibility in selecting a desired coating substance for use with a particular patient. Conventionally, stents are coated by either the stent manufacturer or a third party prior to delivering the stent to a physician for implantation into a patient. In accordance with the present invention, a physician can apply a coating on a bare stent, centrifuge the stent using a small, portable centrifuge device, and implant the freshly-prepared stent in a patient's body. This enables the physician to precisely select the composition of the coating substance applied to the stent. In addition, because the stent can be locally coated and then immediately implanted by the physician after coating, perishable or environmentally-sensitive materials may be used to coat the stent.

EXAMPLE 1

An ACS Duet® stainless steel stent 206, produced by Guidant Corp. of Indianapolis, Ind., is partially dipped or immersed (e.g., for a few seconds or up to 20 seconds or more) in a coating substance composed of BioSpan® (a polyurethane) and Trapidil (i.e., triazolopyrimidine, an anti-platelet) in a 3:1 ratio. The stent 206 is then immediately mounted into a centrifuge container 112, as described above with respect to FIGS. 1-4. The centrifuge container 112 is inserted into chamber 110 and rotated for 30 seconds at 2500 rpm.

The stent 206 is then removed from the centrifuge container 112, placed on a mandrel, and loaded into a Blue M model vacuum convection oven from the Blue M Electric company of Watertown, Wis., for 24 hours at a temperature of 50° C. The heating causes the coating substance to fully dry, leaving a thin coating of BioSpan® and Trapidil on a portion of the stent.

Next, the immersion, centrifugation, and heating acts are repeated on the uncoated portion of the stent 206. For these subsequent processes, the uncoated portion of the stent is dipped or immersed in Duraflo® heparin solution (manufactured by Baxter, Deerfield, Ill.; referenced herein after as "Duraflo®").

The above-described process results in a physically separated, selective coating of two different biologically active agents on the stent.

EXAMPLE 2

Multi-Link Duet™ stents, produced by Guidant Corp. of Indianapolis, Ind., are cleaned in an ultrasonic bath of isopropyl alcohol for 20 minutes, then air dried. An ethylene vinyl alcohol (EVAL) stock solution is made having an EVAL:DMSO:THF w/w ratio of 1:2:1.5. The mixture is placed in a warm water shaker bath at 60° C. for 12 hours. The solution is mixed, then cooled to room temperature. A 9% by weight Dexamethasone solution is formulated as follows: 0.91 grams of the EVAL:DMSO:THF solution is mixed with 0.09 grams of Dexamethasone. The cleaned Multi-Link Duet™ stents are mounted in a makeshift holder placed within ependorf tubes. One half of the stent is dipped in the EVAL-Dexamethasone solution and transferred to the ependorf tube. The dipped end is vertically lower and resting on the holder in the tube. The tube is then centrifuged at 3000 rpm for 60 seconds. The half-coated stent is dried for 2 hours in a vacuum oven at 50° C. Following drying, the clean half of the stent is dipped in Duraflo® (organic soluble heparin) made at 10% w/w in Freon. The coating process is repeated. The final coating configuration results in a one-half Dexamethasone and other one-half Heparin-coated stent.

EXAMPLE 3

Multi-Link Duet™ stents are cleaned in an ultrasonic bath of isopropyl alcohol for 20 minutes, then air-dried. An ethylene vinyl alcohol (EVAL) stock solution is made having an EVAL:DMSO:THF w/w ratio of 1:2:1.5. The mixture is placed in a warm water shaker bath at 60° C. for 12 hours. The solution is mixed, then cooled to room temperature. A 5% by weight Actinomycin-D (Ac-D) solution is formulated as follows: 0.95 grams of the EVAL:DMSO:THF solution is mixed with 0.05 grams of AcD. The cleaned Multi-Link Duet™ stents are mounted in a makeshift holder placed within ependorf tubes. One half of the stent is dipped in the EVAL-AcD solution and transferred to the ependorf tube. The dipped end is vertically lower and resting on the holder in the tube. The tube is then centrifuged at 3000 rpm for 60 seconds. The half-coated stent is dried for 2 hours in a vacuum oven at 50° C. Following drying, the clean half of the stent is dipped in Duraflo® (organic soluble heparin) made at 10% w/w in Freon. The coating process is repeated. The final coating configuration results in a one-half AcD and one-half Heparin-coated stent.

EXAMPLE 4

Multi-Link Duet™ stents are patterned with microdepots on the outer diameter of the stents. Microdepot stents are cleaned in an ultrasonic bath of isopropyl alcohol for 20 minutes, then air dried. A 10% AcD stock solution is made having an AcD:THF w/w ratio of 10:90. A 10% Dexamethasone stock solution is made having a Dexamethasone:THF w/w ratio of 10:90. The cleaned Multi-Link Duet™ stents are mounted in a makeshift holder placed within ependorf tubes. One half of the stent is dipped in the AcD solution and is transferred to the ependorf tube. The dipped end is vertically lower and is resting on the holder in the tube. The tube is then centrifuged at 2000 rpm for 60 sec. The half-coated stent is dried for 1 hour in a vacuum oven at 30° C. Following drying, the clean half of the stent is dipped in the Dexamethasone solution. The coating process is repeated. The drug loaded stents are then coated with Duraflo® solution by spraying a solution of Duraflo® as described in previous embodiments. The final coating configuration results in a one-half AcD and other one-half Dexamethasone coated microdepot stent that is topcoated with Heparin.

The rotational speed during centrifugation can be varied. Higher RPM values may provide improved uniformity and a reduction in defects. However, lower RPM values may improve solid uptake, i.e., the total loading of the coating substance onto stent 206. The solid uptake is calculated by measuring the initial weight of stent 206, and then measuring the weight after the loading and centrifugation acts. Increasing the total centrifugation time may also improve the uniformity and reduce defects in the coating. Accordingly, practitioners should tailor the process to the particular application.

Various embodiments of the described method enable highly viscous materials to be coated onto implantable devices. Viscous materials are not usually amenable to conventional coating methods such as dipping or spraying, because of the viscous material's propensity to accumulate in an uneven layer. However, the addition of a centrifugation step after dipping the implantable device in the viscous coating material can transform the uneven masses into a smooth, even coating.

Embodiments of the method also enable uniform coatings to be applied to implantable devices with improved repeatability, thereby improving coating uniformity between batches of implantable devices. With conventional manually-applied spray-coating techniques, operator error or inconsistency may result in different coating thicknesses between batches of stents. The centrifugation processes can reduce unwanted gross deposition of coating substances and enable high reproducibility of the coating quality.

Embodiments of the method also enable multiple stents to be processed simultaneously. Unlike manually-applied airbrush coating methods, in which stents are coated individually or in small groups, large batches of stents can be simultaneously immersed in the coating solution, simultaneously rotated in the centrifuge device, and simultaneously heated in an oven, thereby increasing throughput.

Embodiments of the method also may improve operator safety when coating implantable devices with hazardous materials. It is generally not desirable to spray coat an implantable device with toxic or radioactive coating substances, because of the increased exposure of the operator to the airborne hazardous coating substance. Dipping and centrifuging the implantable device as described above can decrease the amount of handling required for the coating process, resulting in reduced environmental contamination.

Embodiments of the method may also mitigate defects due to handling of the implantable device. In conventional spray processes, the implantable device is held aloft using one or two clamps or fixtures while the coating substance is sprayed onto the device. The point where these clamps contact the device may be masked from receiving the spray, resulting in defects in the coating. In contrast, the centrifuge container 112 has minimal contact with the implantable device during the centrifuge process.

In general, the coating substance of the various embodiments can have a viscosity within the range of about 0.5 cp to 1,000 cp (centipoise) (whereby 1 cp is approximately equal to the viscosity of water at 20° C.). As such, 0.5 cp approximately represents a very thin substance, 100 cp approximately represents, for example, a light oil, and 1,000 cp approximately represents a thick, viscous substance. Further, the relationship between the centrifugal force of the centrifuge or similar device and the viscosity of the coating substance can be approximately represented by the following equation:

$$U \sim (g + r^* f^2)/k^* m$$

Where:
U=velocity
g=gravitational acceleration
r=average distance*$4\Pi^2$
f=rpm
k=surface area to volume ratio (and other geometric constants/parameters)
m=kinetic viscosity In addition to the above, the viscosity of the coating substance is also dependent on the type of polymer and concentration of polymer contained in the coating substance.

The above embodiments only illustrate the principles of this invention and are not intended to limit the invention to the particular embodiments described. For example, the heating to evaporate the solvent material may be omitted, and other embodiments utilizing centrifugation coating methods can be used in combination with other acts in different processes which do not require active heating. These and various other adaptations and combinations of features of the embodiments disclosed are within the scope of the invention, as defined by the following claims.

We claim:

1. A stent, comprising:
   a first outer surface segment extending from a distal edge of the stent towards a proximal end of the stent and a second outer surface segment extending from a proximal edge of the stent towards a distal end of the stent;
   a uniform first coating layer comprising a drug blended with a polymer evenly distributed over the entire first outer surface segment of the stent but not distributed over the second outer surface segment of the stent, the first coating layer being free of webbing over the first outer surface segment; and
   a uniform second coating layer different from the first coating layer comprising a drug blended with, a polymer evenly distributed over the entire second outer surface segment of the stent but not distributed over the first outer surface segment of the stent, the second coating layer being free of webbing over the second outer surface segment, wherein the second coating layer does not cover the first coating layer.

2. The stent of claim 1, wherein the drug of the first or second coating is for the treatment of restenosis.

3. The stent of claim 1, wherein the first coating is separated from the second coating by a distance along the length of the stent.

4. The stent of claim 1, wherein the drug of the first coating is different from the drug of the second coating.

5. The stent of claim 4, wherein the drug of the first coating or the drug of the second coating is in a class of therapeutic substances selected from the group consisting of antineoplastic, antimitotic, anti-inflammatory, antiplatelet, anticoagulant, antifebrin, antithrombin, antiproliferative, antibiotic, antioxidant and antiallergic substances.

6. The stent of claim 1, further comprising a third coating covering at least a portion of the first and/or second coating.

7. The stent of claim 1, wherein the polymer of the first coating layer is the same as the polymer of the second coating layer.

8. A stent, comprising:
   a body having a first segment and a second segment along a length of the body;
   a uniform first coating layer comprising a first substance evenly distributed along the entire first segment of the body, the first coating layer being free of webbing along the first segment, the second segment being free from the first coating layer; and
   a uniform second coating layer comprising a second substance evenly distributed along the entire second segment of the body, the second coating layer being free of webbing along the second segment, the first segment being free from the second coating layer,
   wherein the second coating layer does not cover the first coating layer, wherein the body is a cylindrical body such that the first segment includes an outer face of the cylindrical body extending from a proximal edge of the stent towards a distal end region of the stent and the second segment includes an outer face of the cylindrical body extending from a distal edge of the stent towards a proximal end region of the stent; and
   wherein each of the first substance and the second substance comprises a drug blended with a polymer, and the first substance and the second substance are different.

9. The stent of claim 8, wherein the polymer of the first substance is different than the polymer of the second substance.

10. The stent of claim 8, wherein the drug of the first substance is different than the drug of the second substance.

11. The stent of claim 8, wherein the first coating comprises a polymer and the second coating comprises the same polymer as the first coating.

* * * * *